US009127319B2

(12) United States Patent
Bardelli et al.

(10) Patent No.: US 9,127,319 B2
(45) Date of Patent: Sep. 8, 2015

(54) MLK4 GENE, A NEW DIAGNOSTIC AND PROGNOSTIC MARKER IN CANCERS

(76) Inventors: Alberto Bardelli, Turin (IT); Miriam Martini, Turin (IT)

( * ) Notice: Subject to any disclaimer, the term of this patent is extended or adjusted under 35 U.S.C. 154(b) by 0 days.

(21) Appl. No.: 13/704,784

(22) PCT Filed: Jun. 15, 2010

(86) PCT No.: PCT/IB2010/052684
§ 371 (c)(1),
(2), (4) Date: Jan. 25, 2013

(87) PCT Pub. No.: WO2011/158061
PCT Pub. Date: Dec. 22, 2011

(65) Prior Publication Data

US 2013/0136755 A1 May 30, 2013

(51) Int. Cl.

| | |
|---|---|
| ***C12Q 1/68*** | (2006.01) |
| ***C07K 16/40*** | (2006.01) |
| ***C12N 15/113*** | (2010.01) |
| ***G01N 33/574*** | (2006.01) |

(52) U.S. Cl.
CPC .............. *C12Q 1/6886* (2013.01); *C07K 16/40* (2013.01); *C12N 15/1137* (2013.01); *C12Y 207/11* (2013.01); *G01N 33/57415* (2013.01); *G01N 33/57419* (2013.01); *G01N 33/57423* (2013.01); *G01N 33/57446* (2013.01); *C12N 2310/14* (2013.01); *C12Q 2600/106* (2013.01); *C12Q 2600/156* (2013.01); *C12Q 2600/158* (2013.01)

(58) Field of Classification Search
CPC ........... C12Q 1/6886; C12Q 2600/156; C12Q 1/485; C12Q 2600/158; C12N 9/1205
See application file for complete search history.

(56) References Cited

U.S. PATENT DOCUMENTS 6,861,239 B1 * 3/2005 Blumenberg et al. ......... 435/194

OTHER PUBLICATIONS

Martini et al., Poster P26. SIBBM Seminar “Frontiers in Molecular Biology” Padua, Jun. 5, 2010.*

* cited by examiner

*Primary Examiner* — Daniel C Gamett
(74) *Attorney, Agent, or Firm* — Nixon & Vanderhye P.C.

(57) ABSTRACT

An in vitro diagnostic method for determining invasive potential of cancer comprising measuring MLK4 gene expression in a cancer cell sample, wherein MLK4 gene overexpression is indicative of an invasive cancer, preferably a colorectal, bladder, breast, gastric, melanoma, lung, ovary or GMB cancer.

10 Claims, 12 Drawing Sheets

Figure 1 a

| Tumor type | Nt change (cDNA) | Aa change (Protein) | Exon | Mutation type | Conserved residue | Ref |
|---|---|---|---|---|---|---|
| CRC | c. C781T | p. H261Y | 1 | Missense | x | 5 |
| CRC | c. C783G | p. H261Q | 1 | Missense | x | 5 |
| CRC | c. G872A | p. G291E | 2 | Missense | x | 5 |
| CRC | c. C878A | p. A293E | 2 | Missense | x | 5 |
| CRC | c. G888A | p. W296Stp | 2 | Nonsense | x | 5 |
| CRC | c. C1408T | p. R470C | 5 | Missense | x | 5 |
| CRC | c. C1408T | p. R470C | 5 | Missense | x | 5 |
| CRC | c. C1657T | p. R553Stp | 6 | Nonsense | x | 5 |
| GBM | c. C1663T | p. R555Stp | 6 | Nonsense | x | (This study) |
| CRC | c. A1787T | p. N596I | 7 | Missense | x | 5 |
| CRC | c. A1885G | p. K629E | 8 | Missense | | 5 |
| GBM | c. C2788T | p. P843S | 9 | Missense | | (This study) |
| GBM | c. A2669C | p. H890P | 9 | Missense | | 6 |
| GBM | c. T2681C | p. M894T | 9 | Missense | | 6 |

b

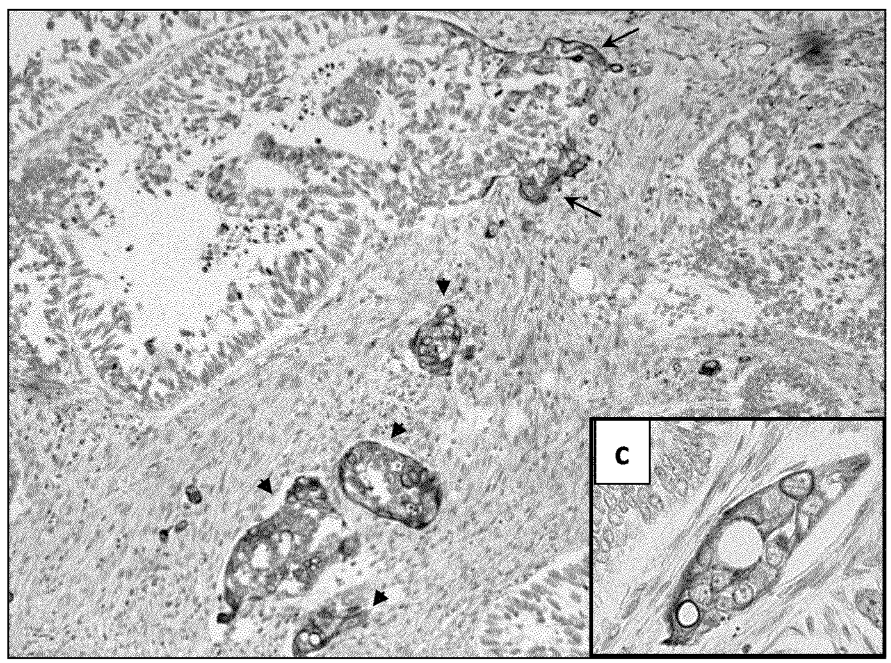

Figure 1/cont.
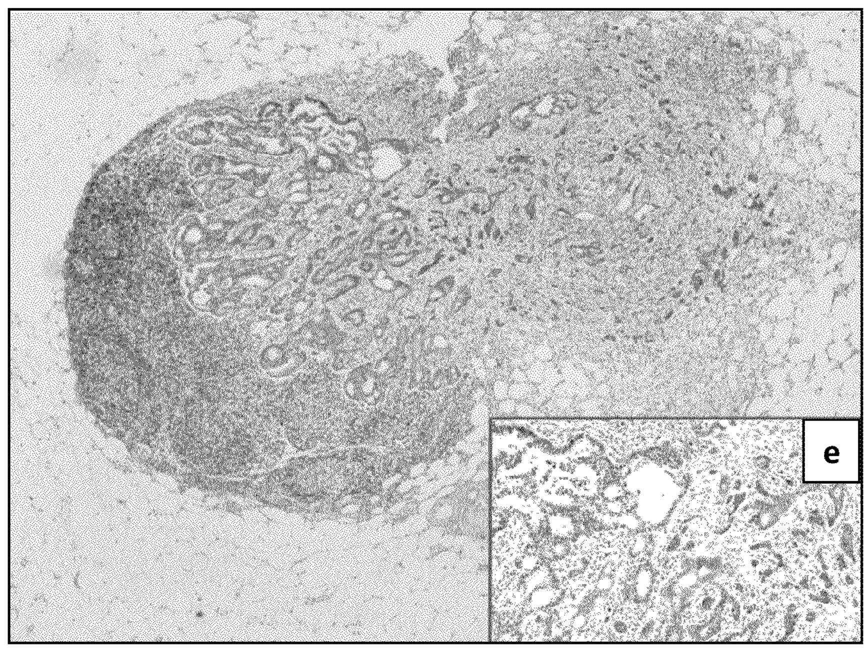
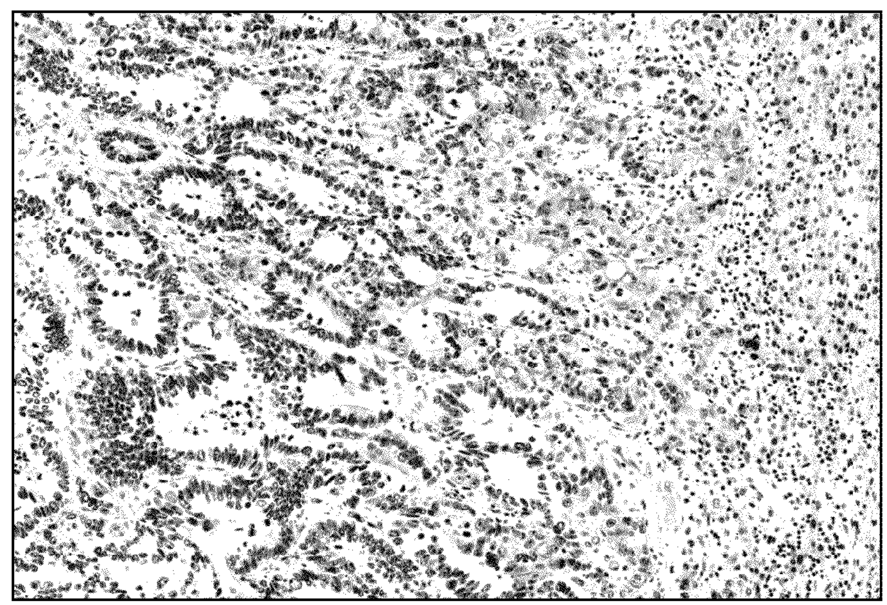

Figure 2
A
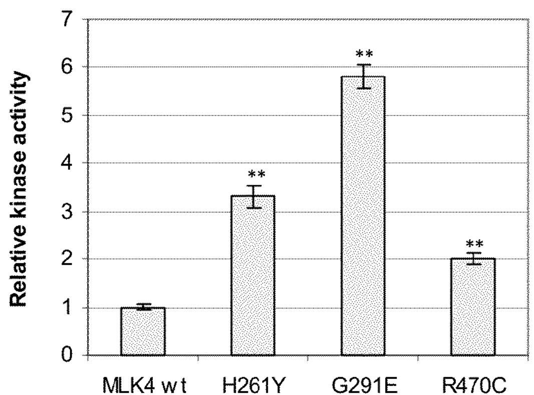
B
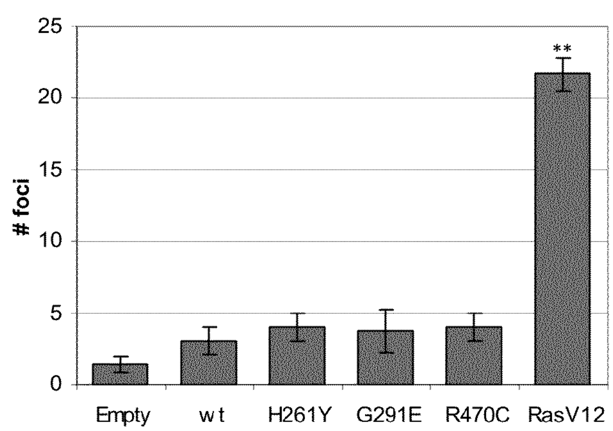
C
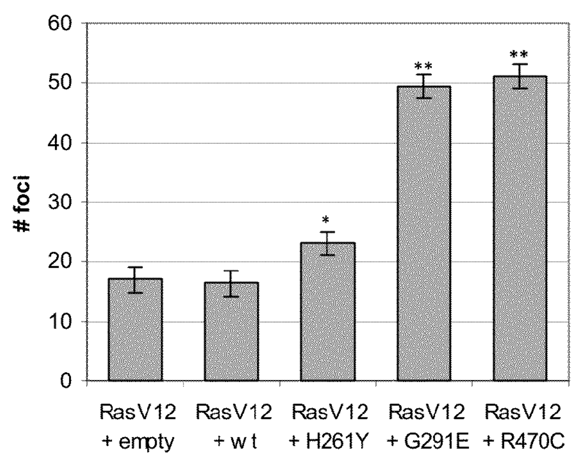

Figure 2/cont.
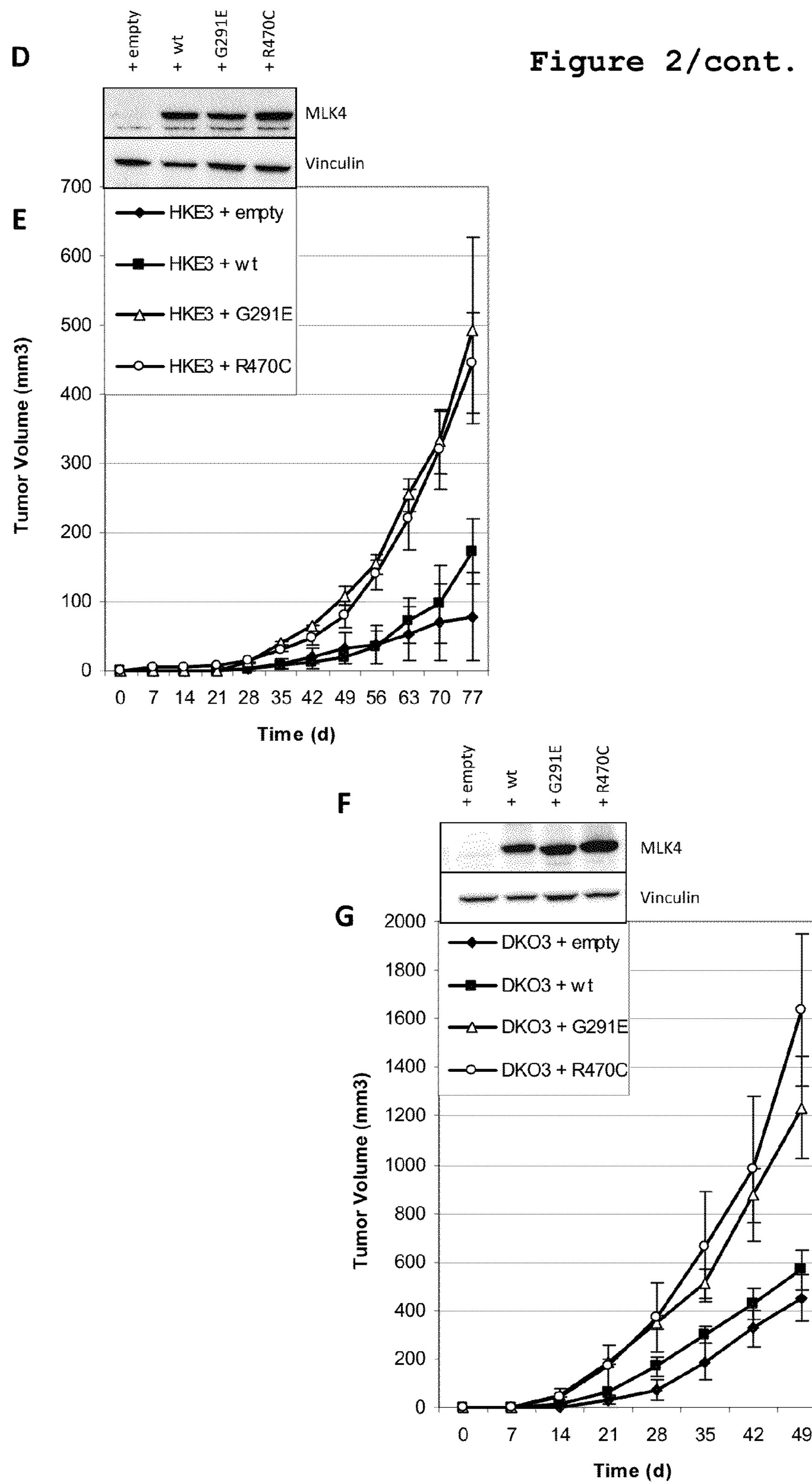

Figure 3
A
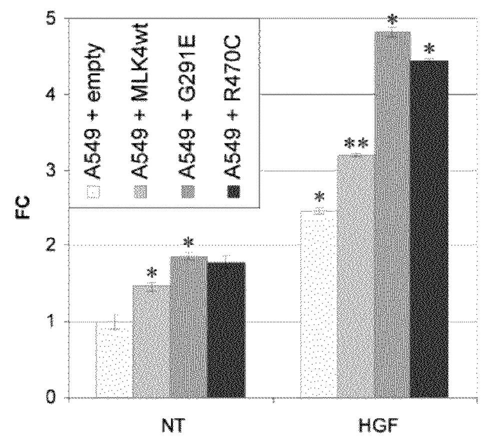
B
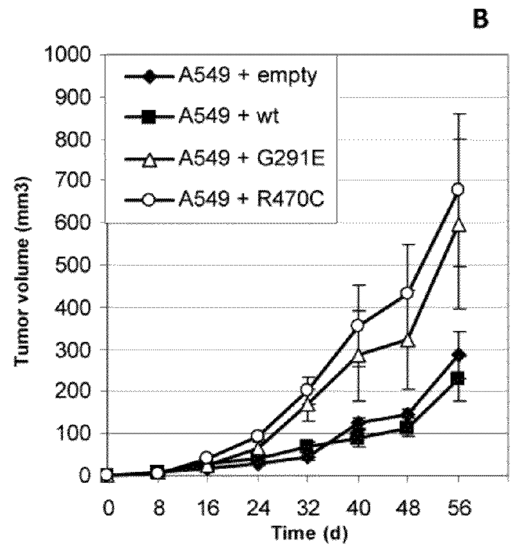
C
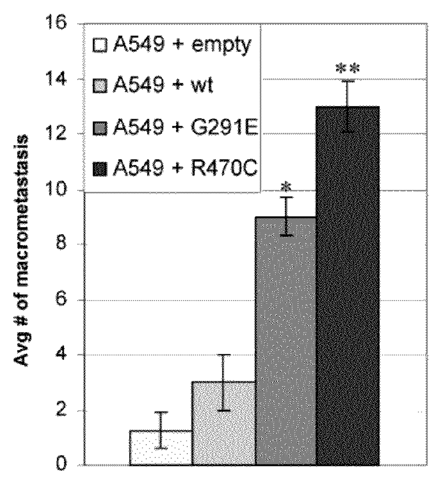
D
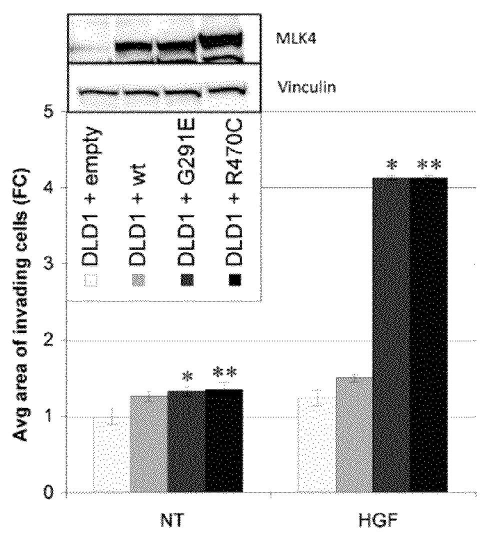

Figure 3/cont.
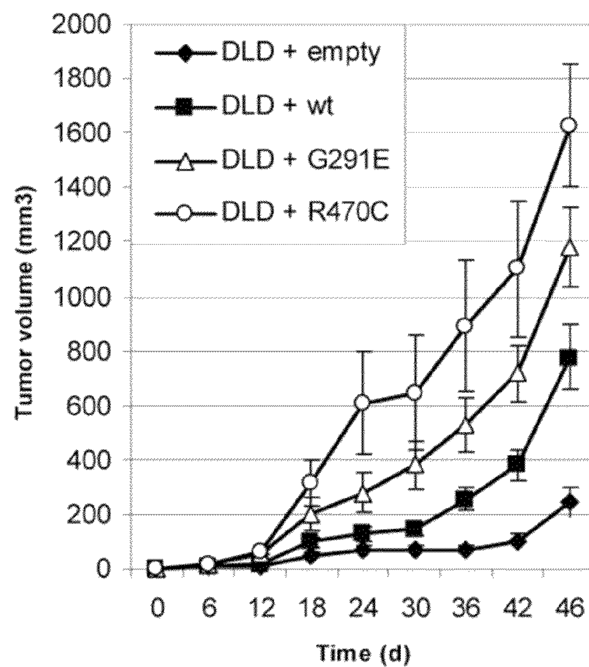
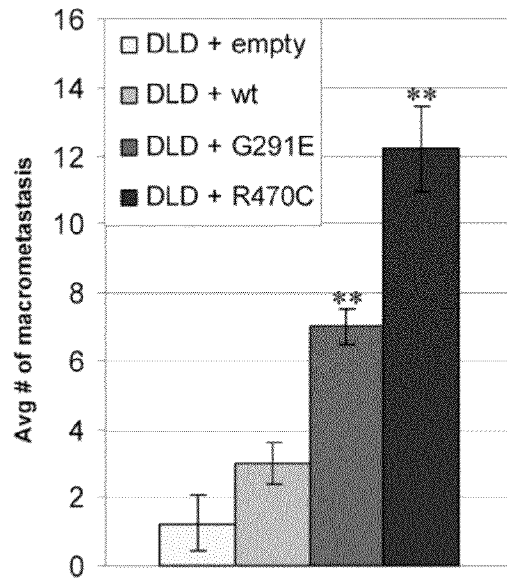

Figure 4
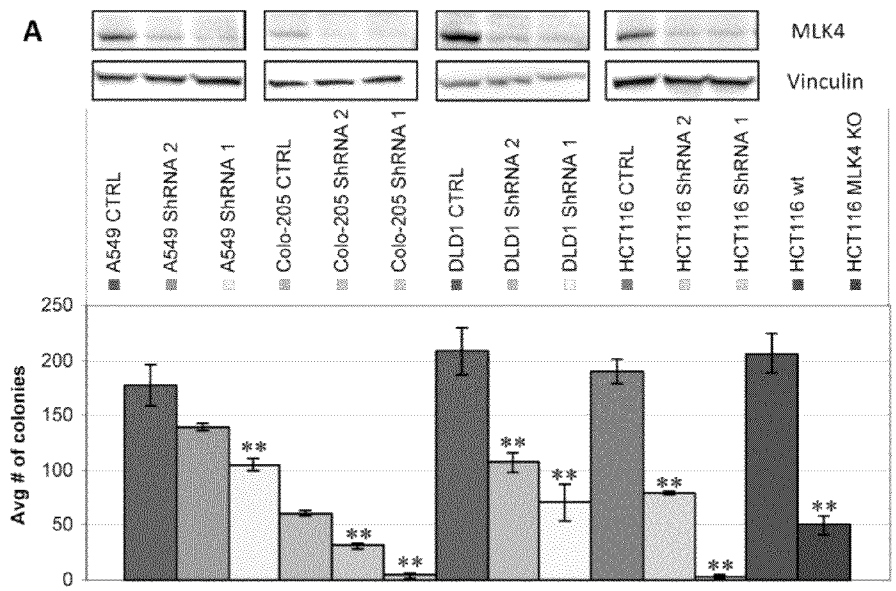
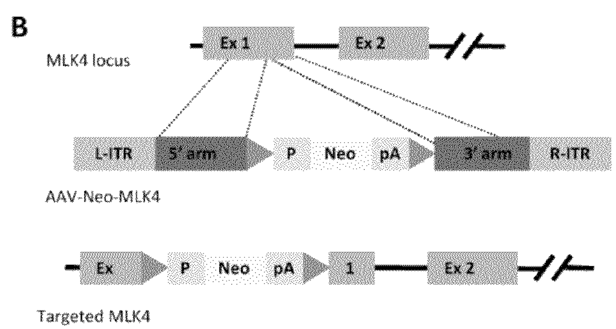
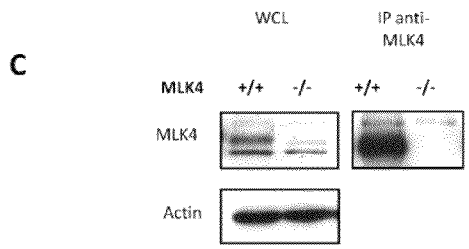

Figure 4/cont.
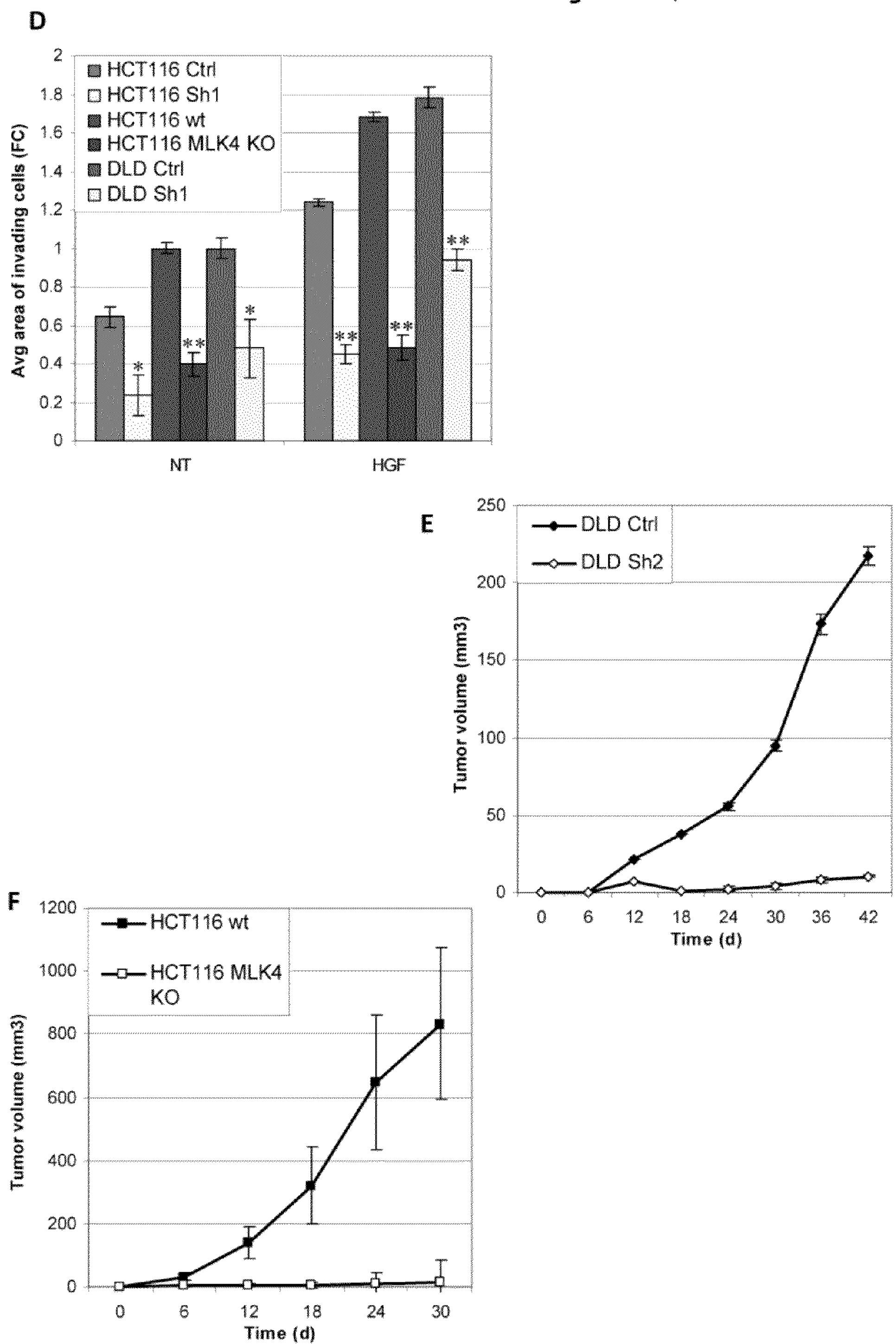

Figure 5
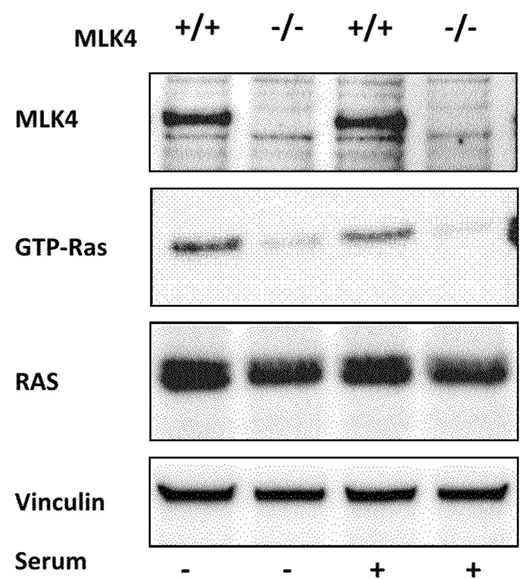
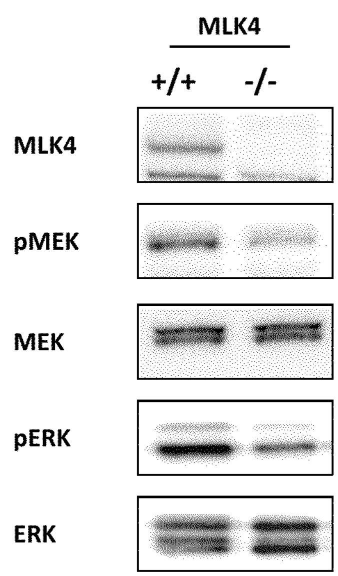

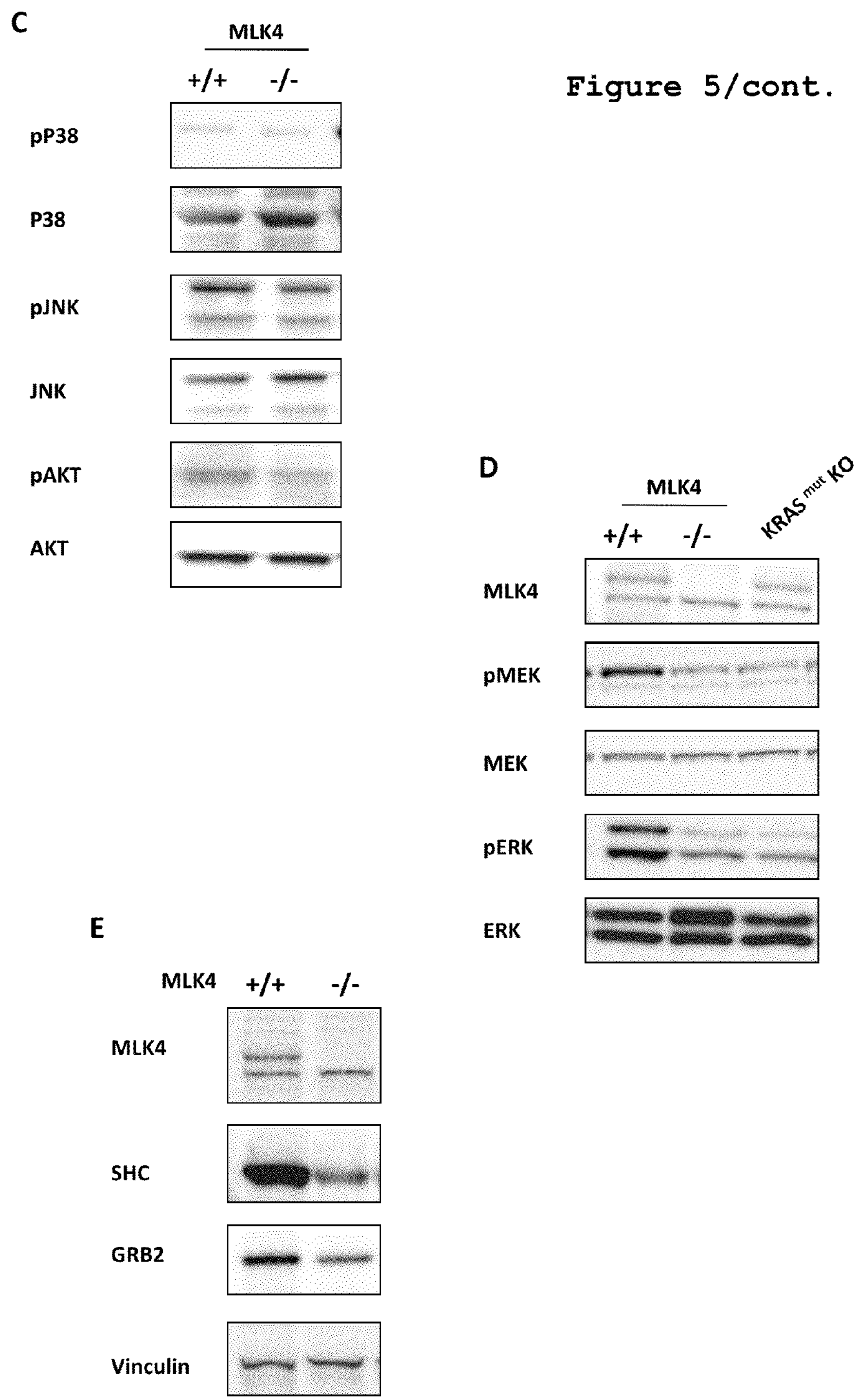
C
MLK4
+/+
-/-
pP38
P38
pJNK
JNK
pAKT
AKT
Figure 5/cont.
D
MLK4
+/+
-/-
KRAS mut KO
MLK4
pMEK
MEK
pERK
ERK
E
MLK4
+/+
-/-
MLK4
SHC
GRB2
Vinculin Figure 6
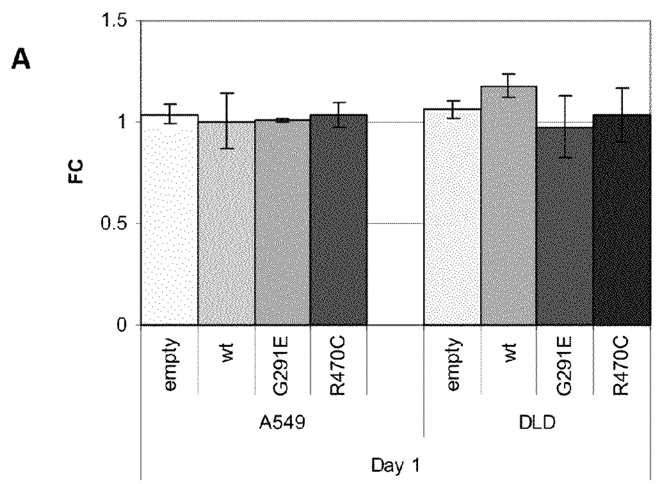
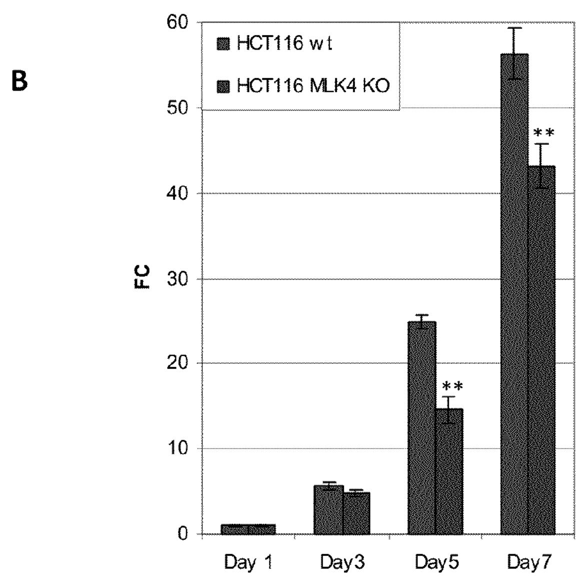
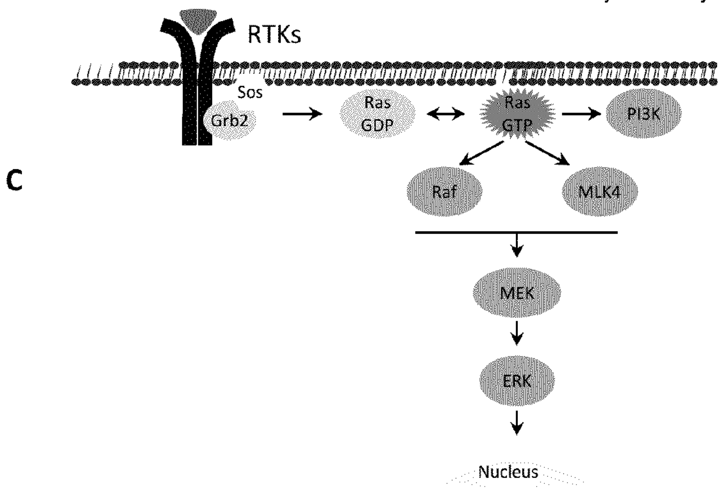

MLK4 GENE, A NEW DIAGNOSTIC AND PROGNOSTIC MARKER IN CANCERS

This application is the U.S. national phase of International Application No. PCT/IB2010/052684, filed 15 Jun. 2010, which designated the U.S., the entire contents of which is hereby incorporated by reference.

TECHNICAL FIELD OF THE INVENTION

The present disclosure concerns the identification of a new diagnostic and prognostic marker in cancers. More specifically, such a new marker belongs to the family of Mixed Lineage Kinases (MLKs). This marker plays a central role in the diagnosis, prognosis and the response to therapy of tumors bearing mutations in the KRAS and BRAF genes. Such tumors are characterized by an extremely poor prognosis and lack of response to therapy.

BACKGROUND ART

Targeting of deregulated protein kinases has proven effective for multiple cancers types. Using high-throughput mutational profiling of kinase genes, we previously identified somatic mutations in Mixed Lineage Kinase 4 (MLK4) in colorectal tumors (CRC) (1). MLK4 belongs to the family of MLK serine-threonine kinases thought to activate multiple intracellular signaling pathways. They are characterized by an amino-terminal SRC-homology domain (SH3), followed sequentially by a kinase domain, a leucine-zipper region and a Cdc42/Rac Interactive Binding (CRIB) motif The carboxyl terminus of all MLKs is proline-rich but diverge significantly among different members of the family, indicating that these regions might serve different regulatory functions. The discovery of MLK4 somatic mutations in CRCs suggests that this kinase may be relevant for tumour initiation and development. Nothing is presently known about the biochemical and cellular properties of MLK4 in normal and neoplastic cells.

SUMMARY OF THE INVENTION

Object of the present invention is the provision of a new diagnostic and prognostic marker in cancers.

According to the present invention said object is achieved thanks to the solution having the characteristics referred to specifically in the ensuing claims. Thus the claims form integral part of the technical teaching herein provided in relation to the present invention.

To achieve this object, the present inventors have developed an in vitro diagnostic method which by measuring of MLK4 gene expression, more specifically MLK4 gene overexpression in a cancer cell sample material is able to determine the potential of invasiveness of the cancer.

In an embodiment, the present disclosure concerns measuring MLK4 protein expression and/or MLK4 coding nucleic acid, preferably RNA, expression.

In a further embodiment, the present disclosure concerns measuring MLK4 gene overexpression in a bioptic sample, wherein the bioptic sample corresponds to the invasive portion of the cancer cell sample material.

In a further embodiment, the present disclosure concerns measuring wild-type MLK4 and/or mutated MLK4 gene expression, wherein the mutated MLK4 gene contains i) at least one somatic mutation at the amino acid level coding for at least one amino acid mutation selected from H261Y, H261Q, G291E, A293E, W296Stp, R470C, R553Stp, R555Stp, N596I, K629E, P843S, H890P, and M894T mutations or ii) at least one somatic mutation at the nucleic acid level selected from C781T, C783G, G872A, C878A, G888A, C1408T, C1657T, C1663T, A1787T, A1885G, C2788T, A2669C, T2681C mutation.

In a still further embodiment, the present disclosure concerns an in vitro diagnostic method, wherein the MLK4 gene expression measurement is performed using a reagent able to selectively bind to MLK4 protein and/or MLK4 coding nucleic acid, which is directly or indirectly labeled with a detectable substance.

In a further embodiment, the present disclosure concerns an in vitro diagnostic method, wherein the MLK4 gene expression measurement is performed in combination with the KRAS gene mutations and expression measurement.

In a further embodiment, the present disclosure concerns inactivation of the MLK4 protein expression or its biochemical function as a mean to therapeutically treat tumors bearings KRAS gene mutations.

BRIEF DESCRIPTION OF THE DRAWINGS

The present invention will now be described in detail in relation to some preferred embodiments by way of non limiting examples, referring to the annexed figures, in which:

FIG. 1. Analysis of MLK4 in human tumors. A) Somatic mutations identified in the MLK4 gene in CRCs and glioblastomas. B) Moderately-differentiated infiltrating colorectal carcinoma. Several neoplastic glandular structures that vary in size and shape can be seen. At the lateral border (identified by arrows) the tumor cells show intense membrane and submembrane staining showing infiltration. The arrowheads indicate areas of strong MLK4 expression in neoplastic cells that are infiltrating the stroma. Note that noninfiltrating cells are negative or show weak apical staining C) High magnification of the section presented in B. D) Metastasis of CRC in a regional lymph node. The fat tissue surrounding the lymph node is infiltrated by the metastatic cells. E) Higher magnification of the section presented in C. F) Liver metastasis of colorectal carcinoma. Only the cells at the periphery of the metastatic nodule (right side) are immunostained.

FIG. 2. Functional interaction between oncogenic RAS and MLK4 on transformation, tumor growth and response to therapy. A) Relative kinase activity of MLK4 wt and mutant alleles. The relative kinase activity was calculated as the ratio between total MLK4 protein and the amount of ATP consumption. Results were normalized using the relative activity of wt MLK4. B) Focus forming assay in NIH3T3 cells transfected with wt and mutant MLK4 alleles. Ras (V12) is used as a positive control. p value≤0.01; error bars represent s.d. C) Focus forming assay in NIH3T3 cells co-transfected with mutant Ras (V12) and wt/mutant MLK4 alleles. p value≤0.01; error bars represent s.d. D) Biochemical validation of HKE3 cancer cells expressing the indicated MLK4 variants. E) Tumor formation by HKE3 cancer cells in xenograft mouse models expressing the indicated MLK4 variants. Cells were injected in the side of nude mice and tumor growth was measured at the indicated time points. Error bars represent s.e.m. F) Biochemical validation of DKO3 cancer cells expressing the indicated MLK4 variants. G) Tumor formation by DKO3 cancer cells expressing the indicated MLK4 variants in xenograft mouse models. Cells were injected in the side of nude mice and tumor growth was measured at the indicated time points. Error bars represent s.e.m.

FIG. 3. Invasive, tumorigenic and metastatic potential of MLK4 mutated alleles. A) A549 cancer cells lines were transduced with lentiviral vectors expressing wild type or two MLK4 mutants. MLK4 expression levels were assessed by western blotting on lysates of cell transduced with empty vector or the indicated constructs. The invasive potential was assessed by migration through a matrigel coated membrane in absence or upon stimulation with Hepatocyte Growth Factor (HGF). *p value≤0.05; p value≤0.01; error bars represent s.d. B) Tumor formation by A549 cancer cells expressing wild type or two MLK4 mutants in xenograft mouse models. Cells were injected in the side of nude mice and tumor growth was measured at the indicated time points. Error bars represent s.e.m. C) Upon sacrifice the lungs were labeled by airway perfusion with the India ink, and superficial metastases were counted under a stereoscopic microscope. p value≤0.01; error bars represent s.e.m. D) Invasive potential of transduced DLD1 tumor cell line. Experiments were performed as in A. *p value≤0.05; p value≤0.01; error bars represent s.d. E) Tumor formation by DLD1 cancer cells expressing wild type or two MLK4 mutants in xenograft mouse models. Experiments were performed as in B. Error bars represent s.e.m. F) Analysis of DLD1-derived superficial lung metastases. Experiments were performed as in C. p value≤0.01; error bars represent s.e.m.

FIG. 4. Downregulation or abrogation of MLK4 expression impairs the transforming and invasive potential of human cancer cells. A) Two independent ShRNAs targeting the MLK4 gene were used to downregulate MLK4 expression in multiple cell lines (A549, Colo205, DLD1, HCT116) from different tumor types. Expression levels of the MLK4 protein were assessed by western blotting. Anchorage-independent growth (soft agar) assay performed on parental and MLK4 knock down/knock out cells. *p value≤0.05; **p value≤0.01; error bars represent s.d. B) Schematic representation of the vector used to KO the MLK4 genes from the genome of the HCT116 cell line. A sequential targeting strategy was used to knock out (KO) both of the MLK4 alleles. L-ITR: Left-Inverted Terminal Repeats, P: neomycin promoter, Neo: neomycin resistance cassette, pA: polyadenilation sequence, R-ITR: Right-Inverted Terminal Repeats. C) Expression levels of the MLK4 protein assessed by western blotting in parental and knock out HCT116 cells. D) The invasive potential of parental and MLK4 knock-down or KO cells was assessed by migration through a matrigel coated membrane in absence or upon stimulation with Hepatocyte Growth Factor (HGF). *p value≤0.05; **p value≤0.01; error bars represent s.d. E) Control and MLK4 knock-down DLD1 cancer cells were injected in the side of nude mice and tumor growth was measured at the indicated time points. Error bars represent s.e.m. F) Control and MLK4 knock-out HCT 116 cancer cells were injected in the side of nude mice and tumor growth was measured at the indicated time points. Error bars represent s.e.m.

FIG. 5. Effects of MLK4 abrogation on the KRAS-ERK signaling pathway. A) Measurement of 'active' (GTP bound) RAS assessed by a pull-down assay with the RAS binding domain of C-RAF in parental and MLK4 knock out cells in the absence or presence of serum. Total RAS is used as a reference for sample loading. B) Biochemical analysis of MEK1/2 and ERK1/2 kinases phosphorylation levels. Cell lysates were subjected to western blotting with the indicated antibodies. C) Biochemical analysis of p38, SAPK/JNK and AKT kinases phosphorylation levels. Cell lysates were subjected to western blotting with the indicated antibodies. D) Comparison of MEK1/2 and ERK1/2 kinases phosphorylation levels in parental, MLK4 knock out and mutant KRAS KO HCT116 cells. E) Analysis of the level of expression of SHC and Grb2 adaptor proteins detected by western-blot analysis in parental and MLK4 knock out HCT116 cells.

FIG. 6. A) Rates of cell proliferation of A549 and DLD1 cells transduced with wt and mutant MLK4. Error bars represent s.d. B) Cell proliferation rates of parental and MLK4 KO HCT116 cancer cells. *p value≤0.05; **p value≤0.01; error bars represent s.d. C) Schematic representation of the MLK4 signaling pathway according to this work.

DETAILED DESCRIPTION OF EMBODIMENTS OF THE INVENTION

Figure 7:
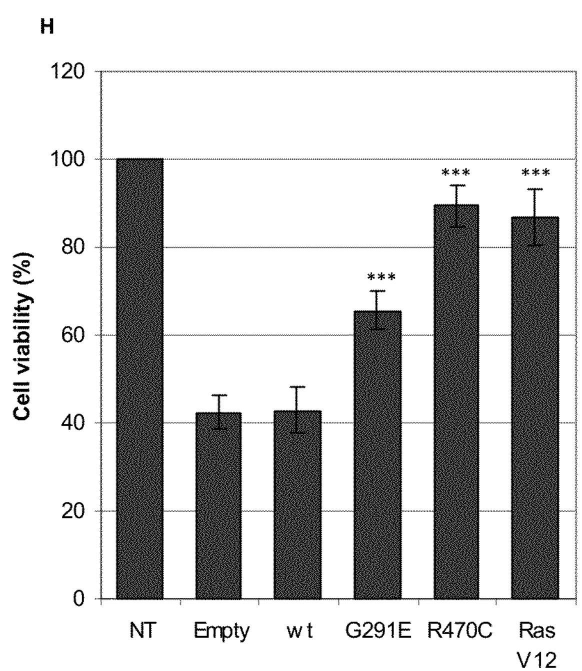
FIG. 7. The colorectal cancer cell line DiFi was transduced with lentiviral vectors expressing wild type or two MLK4 mutants and RAS V12. The indicated cell lines were treated with 0.1 μg/ml of Cetuximab (Erbitux) for 72 hours, after which cell viability was assessed by the ATP assay. Results shown are normalized to untreated cells; ***p value≤0.001; error bars represent s.d.

The present invention will now be described in detail in relation to some preferred embodiments by way of non limiting examples.

In the following description, numerous specific details are given to provide a thorough understanding of embodiments. The embodiments can be practiced without one or more of the specific details, or with other methods, components, materials, etc. In other instances, well-known structures, materials, or operations are not shown or described in detail to avoid obscuring aspects of the embodiments.

The headings provided herein are for convenience only and do not interpret the scope or meaning of the embodiments.

Using molecular analysis of tumor samples combined with biochemical and functional approaches we have assessed the role of MLK4 in cancer cells. We employed two complementary strategies: (i) ectopic expression of wt and mutated MLK4 alleles (forward genetics) and (ii) targeting MLK4 expression using ShRNA-mediated down regulation or somatic gene knock out (KO) of MLK4 gene (reverse genetics) in normal and cancer cell lines.

Mutational profiling of the coding region of the MLK4 gene was performed in multiple tumor types including bladder, breast, gastric, melanoma, lung, ovary and glioblastoma (GBM) samples (Table 1).

TABLE 1

| Tumor type | Histotype | Number of samples analysed |
|---|---|---|
| Bladder | Total | 35 |
| | transitional cell carcinoma | 33 |
| | cell line | 2 |
| Breast | Total | 88 |
| | ductal carcinoma | 26 |
| | lobular carcinoma | 29 |
| | medullary carcinoma | 17 |
| | mucinous carcinoma | 16 |
| Gastric | Total | 12 |
| | adenocarcinoma of gastroesophageal junction | 12 |
| Glioma | Total | 113 |
| | Glioblastoma | 105 |
| | anaplastic astrocytoma | 2 |
| | anaplastic oligodendroglioma | 2 |
| | high grade glioma cell lines | 4 |
| Lung | Total | 86 |
| | Adenocarcinoma | 86 |
| Melanoma | Total | 22 |
| | Primary | 1 |
| | nodal metastasis | 12 |

TABLE 1-continued

| Tumor type | Histotype | Number of samples analysed |
|---|---|---|
| | cutaneous metastasis | 7 |
| | visceral metastasis | 2 |
| Ovary | Total | 48 |
| | serous adenocarcinoma | 48 |

In addition to those previously reported (1) we found novel somatic mutations affecting the MLK4 gene in GBMs (FIG. 1A). Overall, the mutation frequency in CRC and GBMs were 9/192 (5%) and 4/140 (3%), respectively. Most of the non-synonymous mutations involved evolutionarily conserved amino acids some of which were affected multiple times. In addition, a subset of the mutations occurred at amino acids previously shown to be pathogenic in other protein kinases (1). Furthermore, two nonsense mutations were identified that affected arginines R553 and R555 in the C-terminus. It is possible that latter truncating mutations influence the function of MLK4 by removing the putative C-terminal inhibitory domain. Finally, the nonsense mutation (W296 stop), located in the kinase domain, may represent a "passenger", rather than a "driver" mutation.

To assess whether MLK4 deregulation occurred by mechanisms other than somatic mutations, we developed two polyclonal antibodies and used them to measure the expression pattern of MLK4 in CRC samples. Immunohistochemical (IHC) analysis was performed on a panel of 38 CRCs. The results demonstrated that most tumors expressed low or undetectable levels of MLK4 expression. However, 9 CRC samples (24%) showed clear MLK4 positivity, which was very distinctive being limited at the invasive portion of the tumor (FIG. 1B). Areas of intensely stained neoplastic cells were typically observed infiltrating the stroma (FIG. 1C). In contrast, non-infiltrating cells were negative or showed a very weak expression signal. For one sample lymph node and liver metastasis were available in addition to the primary tumour (FIG. 1D-F); in both, MLK4 expression was again confined to the invasive portion of the tumor. DNA sequence analysis excluded that the MLK4 gene was somatically mutated in the CRC samples that demonstrated increased expression. The MLK4 expression pattern suggests that MLK4 plays a central role in tumor invasion.

Lentiviral vectors were engineered to stably transduce MLK4 wt cDNA and two of the mutant alleles, specifically H261Y, G291E and R470C, identified in the CRC sequencing screens (Table 1). The H261Y was selected for further studies since histidine 261 was found mutated twice (H261Y and H261Q). The G291E allele was selected as it is located in a region corresponding to the BRAF V600E oncogenic mutation found in multiple tumor (2). The R470C allele was chosen as this variant has been identified in two independent CRC samples (Table 1).

Biochemical in vitro assay were used to assess the catalytic activity of wt and mutated MLK4. As a recipient for these experiments we used colorectal cancer cells in which the MLK4 gene was genetically inactivated and as a result the endogenous MLK4 protein was absent (see below FIG. 4B). These cells were transduced with wild type or the H261Y, G291E and R470C MLK4 variants. Mutated MLK4 proteins displayed increased kinase activity as compared to the wt counterpart (FIG. 2A).

Next we sought to establish the role of MLK4 on cellular phenotypes associated with tumorigenesis using both forward and reverse genetics strategies. We initially used the standard NIH3T3 focus forming assay to assess the transforming potential of wt and mutated MLK4 alleles. Although a positive control (RAS G12V) was capable of promoting focus formation at high efficiency, no effects were seen when wt or mutated MLK4 were used (FIG. 2B). These results suggest that wt and mutant MLK4 alleles are unable, per se, to support cellular transformation. On the contrary, when mutant MLK4 was co-transfected in NIH3T3 cells with the oncogenic version of RAS (G12V) a striking synergistic effect in focus formation was observed (FIG. 2C). Importantly, two of the mutants (G291E and R470C) but not wild type MLK4 increased the transforming potential of RAS G12V.

This behavior is reminiscent of other cancer genes (such as Pokemon) whose transforming potential becomes detectable only when assessed in cooperation with other oncogenes (3).

To further assess the role of MLK4 in KRAS mediated oncogenesis, we employed an isogenic variant (HKE3) of a tumorigenic human colorectal cancer cell line, HCT116, in which the mutant KRAS allele is disrupted by homologous recombination (4). Consequently, HKE3 cells are a suitable model to establish whether mutated MLK4 alleles can rescue the tumorigenic phenotype of oncogenic KRAS. HKE3 expressing wt or the MLK4 mutants (G291E and R470C) that cooperated with RAS in the transformation assays (FIG. 2D) were subcutaneously injected into nude mice. Cells expressing the empty vector were used as controls. Two weeks after inoculation, HKE3 cells transduced with the empty vector or wt MLK4 did not generated tumors (FIG. 2E). On the contrary mice inoculated with the G291E and R470C MLK4 mutants developed subcutaneous tumors within 2 weeks. The observation that mutated MLK4 alleles rescue the tumorigenic phenotype of cancer cells, in which mutant KRAS was deleted, supports the concept that MLK4 plays a critical role in the same pathway.

To validate this observation in a different cellular system, we used an isogenic variant (DKO3) of another highly tumorigenic human colorectal cancer cell line (DLD-1), in which the mutant KRAS allele has been disrupted by homologous recombination. Similar in vivo experiments were performed in DKO3 cells transduced with MLK4 mutant alleles with comparable results (FIG. 2F-G).

The pivotal role of the KRAS pathway in human cancers has been further underlined by the discovery that KRAS mutated colorectal tumors do not respond to the anti EGFR monoclonal antibodies cetuximab (Erbitux) and panitumumab (Vectibix) (5, WO-A-2008/112274). These findings were rapidly translated into the clinic and detection of KRAS mutations is now routinely used to select patients eligible for cetuximab therapy. We previously reported that the ectopic expression of mutated KRAS and BRAF impairs the response to cetuximab and panitumumab of colorectal cancer cells (6, 7). We reasoned that if MLK4 acts downstream to KRAS its oncogenic activation could also impairs the effects of cetuximab.

To test this hypothesis we used the DiFi colorectal cancer cell line which is inhibited by nanomolar concentration of cetuximab. In DiFi cells the KRAS pathway is activated by amplification/overexpression of the EGFR gene. DiFi cells are wild type for MLK4, KRAS, BRAF, PIK3CA and PTEN mutations, thus representing a suitable model for our experiments. Wt or mutated MLK4 proteins were expressed in DiFi cells and mutated KRAS (G12V) was used as positive control. Cells expressing mutated MLK4 or KRAS alleles were less sensitive to cetuximab as indicated by their markedly increased survival upon treatment with this monoclonal antibody (FIG. 7).

These data indicate that the presence of oncogenic MLK4 can substitute for KRAS mutations in conferring resistance to EGFR targeted therapies, supporting the concept that KRAS and MLK4 are involved in the same signal transduction pathway (FIG. 6D).

We next sought to assess the role of MLK4 alleles in invasive-growth, a genetic program leading to metastasis formation. To formally test this hypothesis, we evaluated whether ectopic expression of wt or mutated MLK4 might affect the invasive properties of cancer cells (A549 and DLD1). Both wt and mutant MLK4 mildly affected cell invasion measured by the matrigel Boyden chamber assays in standard growth medium. We then assessed the invasiveness upon stimulation with the Hepatocyte Growth Factor (HGF) which has previously been linked to the invasive growth properties of cancer cells. In the presence of HGF, expression of both mutated MLK4 alleles (G291E and R470C) markedly increased invasion as compared to the non-transduced cells or those expressing wt MLK4 (FIG. 3A and 3D).To determine whether MLK4 promoted cell proliferation might have contributed to the augmented invasive potential, cell proliferation rates were analyzed. Ectopic expression of MLK4 did not affect proliferation (FIG. 6A).

To further evaluate the tumorigenic potential of MLK4 mutations, A549 and DLD1 cells expressing wt MLK4, G291E and R470C mutants were subcutaneously injected into nude mice. Cells expressing the empty vector were used as controls. Mice inoculated with wt or mutated MLK4 cells developed subcutaneous tumors within 3 weeks. Both A549 and DLD1 cells transduced with mutant MLK4 gave rise to larger tumors compared to control cells (FIGS. 3B and 3E). Metastasis formation in the lungs of mice bearing MLK4 over-expressing tumors was then quantified. We found that the number of metastasis was increased in MLK4 mutant expressing tumors versus controls (FIGS. 3C and 3F) in both A549 and DLD1 models.

When considered together, the forward genetic approaches indicate that mutated MLK4 alleles cooperate or substitute oncogenic KRAS in transformation and invasion and promote metastasis formation.

As a complementary approach, reverse genetics was used to evaluate how reduced expression or deletion of the MLK4 gene affected the tumorigenic properties of cancer cells. We first identified ShRNA that targeted the MLK4 sequence leading to efficient downregulation of its expression. Two independent MLK4 ShRNAs were selected based on their efficiency in reducing MLK4 expression in multiple cell lines derived from colon and lung cancers, including those utilized in the forward genetic approach (FIG. 4A, upper panel). We first investigated the effect of MLK4 down-regulation on anchorage independent growth, a key feature of the neoplastic phenotype. Anchorage-independent growth of all cancer cell lines was significantly reduced or almost completely impaired (FIG. 4A).

Experiments based on ShRNA mediated down regulation may be misleading due to non-specific gene targeting. We therefore used homologous recombination to delete exon 1 (where the MLK4 kinase domain is located) from the HCT116 cells to generate cells with permanently abrogated MLK4 expression (FIG. 4B). A two-step genetic strategy was used to obtain first heterozygous and then homozygous cells in which both alleles of the MLK4 locus were correctly targeted. Knocked out (KO) cells were viable yet lacked MLK4 expression confirmed by PCR and immunoblotting with the anti-MLK4 antibody (FIG. 4C). Soft agar growth of MLK4 KO cells was severely impaired (FIG. 4A) confirming and substantiating the results obtained with the Sh-mediated MLK4-silencing. Similarly, the invasive potential of knocked down and KO MLK4 cells was dramatically impaired (FIG. 4D).

Next, we determined the effect of reduced or abrogated MLK4 expression on the tumorigenic potential in colorectal cancer cells in vivo. To this end we took advantage of DLD1 and HCT116, two colorectal cancer cell lines which harbor a single copy of the activated KRAS oncogene. MLK4 knock down cells and those transduced with scrambled ShRNA were evaluated for the ability to growth in xenograft experiments. When inoculated into nude mice, DLD1 control cells rapidly formed solid tumors while MLK4 knock down cells did not (FIG. 4E). To independently confirm these results we used the HCT116 cell in which MLK4 was genetically deleted. Xenograft experiments showed that cancer cells lacking MLK4 expression were virtually unable to form subcutaneous tumors while the corresponding isogenic wt cells rapidly grew forming large tumor masses (FIG. 4F).

To gain mechanistic insights into the role of MLK4 in RAS signaling, we took advantage of wt and MLK4 KO HCT116 cells which carry constitutively active KRAS (G13D). It has been reported that MLKs are serine/threonine protein kinases that regulate signaling by mitogen-activated-protein kinase (MAPK) pathways. We reasoned that lack of MLK4 could affect different steps of the KRAS-MAPK signaling cascade. We initially analyzed the levels of 'active' (GTP bound) KRAS and the activation (phosphorylation) of its downstream effectors MEK, ERK, JNK, p38 and AKT.

We found that in the absence of MLK4 the amount of active (GTP-bound) RAS and the levels MEK and ERK phosphorylation were reduced (FIGS. 5A and 5B). The absence of MLK4 did not affect the phosphorylation levels of JNK, p38 and AKT (FIG. 5C). Of note, in HCT116 cells the knock out of MLK4 or the deletion of mutant KRAS resulted in comparable reduction of MEK and ERK phosphorylation FIG. 5D). Interesting the reduction of KRAS-MAPK activation in MLK4 knock out cells was accompanied by lower expression of SHC to a less extent Grb2, two known amplifier of the RAS signaling cascade (FIG. 5E).

Together with the functional experiments showing KRAS-MLK4 cooperation in promoting tumorigenesis, these results indicate that the main signaling axis (the ERK/MAPK cascade) activated by oncogenic KRAS is impaired in the absence of the MLK4 kinase.

A key biological output resulting from MAPK activation is the induction of cell proliferation. We therefore evaluated the growing rate of parental and KO MLK4 cells and found that the absence of MLK4 affected the proliferation of HCT116 cells (FIG. 6B). These findings further support the concept that MLK4 is involved in the proliferation of cells that are dependent on mutant KRAS.

This work was prompted by the finding that MLK4 is somatically mutated in CRCs and GBMs. Mutations of the related MLK3 kinase were recently detected in 21% of microsatellite unstable (MSI) colorectal tumors (8). We sequenced the MLK4 exons where we previously detected somatic mutations in 30 MSI colorectal tumors and did not find any mutations.

Mutant alleles of MLK4 and KRAS work in concert to trigger cellular transformation and mutant MLK4 rescues the tumorigenic potential of cells in which mutant KRAS is deleted. When considered together these findings implicate MLK4 in KRAS mediated oncogenesis. Remarkably, knock down or knock out of MLK4 abrogates the growth of cancer cells carrying mutated KRAS.

We and others have previously targeted the MET, KRAS and PIK3CA oncogenes by homologous recombination in HCT116 cancer cells. While targeting of each of these oncogenes drives distinct biological phenotypes, only the deletion of mutated KRAS and MLK4 results in abrogation of tumorigenesis.

In conclusion, these data identify the MLK4 kinase as a novel effector of KRAS, a presently undruggable human oncogene (FIG. 6C). Pharmacological targeting of the MLK4 kinase is amenable and provides a novel therapeutic prospect for KRAS mutated tumors.

Materials and Methods

Mutational Analysis

PCR primers were designed using Primer 3 (http://frodo.wi.mit.edu/cgibin/primer3/primer3_www.cgi), and synthesized by Invitrogen/Life Technologies, Inc. (Paisley, England). The PCR and sequencing primers are listed in Table 2.

TABLE 2

| Exon | Forward primer | Reverse primer | Sequence primer |
|---|---|---|---|
| 1 1_1 | CACCGATCGCGATTCCTAC SEQ ID No.: 1 | TCGAAGGCGACGTGTACC SEQ ID No.: 2 | TCCTACCCCCTCGCCTTC SEQ ID No.: 3 |
| 1_2 | CTCAGCGTCCTCGTCGTC SEQ ID No.: 4 | CGCAGCTCGATGATGTTG SEQ ID No.: 5 | GCAGCTCGATGATGTTGG SEQ ID No.: 6 |
| 1_3 | CATCTTCCCCGCCAACTAC SEQ ID No.: 7 | GGCCCAGTTGACCAGCAC SEQ ID No.: 8 | TCTTCCCCGCCAACTACG SEQ ID No.: 9 |
| 1_4 | CAGGAGGTGGCCGTGAAG SEQ ID No.: 10 | CGCCCTAAGGCTGACTCC SEQ ID No.: 11 | CTCCCACCTCTTTCCATCTG SEQ ID No.: 12 |
| 1_5 | GCACGTGCTGGTCAACTG SEQ ID No.: 13 | CGCCCTAAGGCTGACTCC SEQ ID No.: 14 | ACTGGGCCGTGCAGATAG SEQ ID No.: 15 |
| 2 | CAGGCACAGATAACCCACTAAAG SEQ ID No.: 16 | AAACCATAAAAATTCATTCA AAAAGG SEQ ID No.: 17 | CATGCCACAGAAAAATTGTG SEQ ID No.: 18 |
| 5 | GGGAATTTCAGCTTCTCCTTG SEQ ID No.: 19 | CCCTATCTCTTTCCTGGTTCTG SEQ ID No.: 20 | GGGGTCGCCAGTGTAGTG SEQ ID No.: 21 |
| 6 6_1 | CGATCCTGCAATATTCTTTGC SEQ ID No.: 22 | GTGGCACCTACGAAATGTCC SEQ ID No.: 23 | TTGCTGTGTGCTAAATACATGG SEQ ID No.: 24 |
| 7 7_2 | TTTCTCATTGTTTTCATGTT TTGAG SEQ ID No.: 25 | GCATGATAAATTCATCCTAGAA AATTG SEQ ID No.: 26 | TTTTGAGTAAGGTAGTTTCAC AACTG SEQ ID No.: 27 |
| 8 | TTGTCAGCCCTTCAAAACTG SEQ ID No.: 28 | CTTGCTAATCTCCCCTCTGC SEQ ID No.: 29 | TGGTCTGTATCCACCAAAACC SEQ ID No.: 30 |
| 9 9_1 | GTAAAACGACGGCCAGT GAAAAGGGCTGCATGTGTTT SEQ ID No.: 31 | CTCTCTGAGCATCTTTCCCAA SEQ ID No.: 32 | GTAAAACGACGGCCAGT SEQ ID No.: 33 |
| 9_2 | GCCTACATTGATCTACCTCTTGG SEQ ID No.: 34 | GTAAAACGACGGCCAGT TCTTCTCTTCCTTGGGCAAC SEQ ID No.: 35 | GTAAAACGACGGCCAGT SEQ ID No.: 36 |
| 9_3 | CATAAAGCACAGGCTGCTGA SEQ ID No.: 37 | GTAAAACGACGGCCAGT AGCAGGCACTTTGTGGAGAA SEQ ID No.: 38 | GTAAAACGACGGCCAGT SEQ ID No.: 39 |
| 9_4 | GTAAAACGACGGCCAGT CCACACCTTCTTTCTCCACAA SEQ ID No.: 40 | CATTCCCACATGTCTGCTGT SEQ ID No.: 41 | GTAAAACGACGGCCAGT SEQ ID No.: 42 |
| 9_5 | GTAAAACGACGGCCAGT CAAGAAACTTGCCGTCTTCC SEQ ID No.: 43 | CAAATTATTAAATGTCATCAC CAGGA SEQ ID No.: 44 | GTAAAACGACGGCCAGT SEQ ID No.: 45 |

PCR primers that amplify the selected exons and the flanking intronic sequences, including splicing donor and acceptor regions, were used and PCR products were on average 381 bps in length. PCR was performed in both 384- and 96-well formats in 5- or 10-uL reaction volumes, respectively, containing 0.25 mmol/L deoxynucleotide triphosphates, 1 umol/L each of the forward and reverse primers, 6% DMSO, 1× PCR buffer, 1 ng/uL DNA, and 0.05 unit/uL Platinum Taq (Invitrogen/Life Technologies). A touchdown PCR program was used for PCR amplification (Peltier Thermocycler, PTC-200, MJ Research, Bio-Rad Laboratories, Inc., Italy). PCR conditions were as follows: 94° C. for 2 min; three cycles of 94° C. for 15 s, 64° C. for 30 s, 70° C. for 30 s; three cycles of 94° C. for 15 s, 61° C. for 30 s, 70° C. for 30 s; three cycles of 94° C. for 15 s, 58° C. for 30 s, 70° C. for 30 s; and 35 cycles of 94° C. for 15 s, 57° C. for 30 s, and 70° C. for 30 s, followed by 70° C. for 5 min and 12° C. thereafter. PCR products were purified using AMPure (Agencourt Bioscience Corp., Beckman Coulter S.p.A, Milan, Italy). Cycle sequencing was carried out using BigDye Terminator v3.1 Cycle Sequencing kit (Applied Biosystems, Foster City, Calif.) with an initial denaturation at 97° C. for 3 min, followed by 28 cycles of 97° C. for 10 s, 50° C. for 20 s, and 60° C. for 2 min.

Sequencing products were purified using CleanSeq (Agencourt Bioscience, Beckman Coulter) and analyzed on a 3730 DNA Analyzer, ABI capillary electrophoresis system (Applied Biosystems). Sequence traces were analyzed using the Mutation Surveyor software package (SoftGenetics, State College, PA).

Immunohistochemical Analysis

Paraffin embedded sections were dewaxed, hydrated, treated with proteinase K (DAKO, Glostrup, Denmark) and immunostained using a labelled polymer detection system (Bond Polymer Define Detection, Vision Biosystem, Mount Waverley, Australia) and automated stainer (BOND-maX, Vision BioSystem). The primary polyclonal antibody was used at a dilution of 1:1000. Negative controls were obtained by replacement of primary antiserum with buffer. Only tumors which exhibited intense membrane were categorized as overexpressing MLK4.

DNA Constructs and Mutagenesis

The cDNA encoding for MLK4 set forth in SEQ ID NO.:46 was synthesized by RT-PCR by first inserting into the TopoTA vector. Full-length MLK4 cDNA was subcloned into the pCEV29.1 (10) or into pRRL plasmid (11). Mutants of MLK4 containing point mutations were constructed using the QuikChange II XL Site-directed mutagenesis kit (Stratagene) with MLK4 wt plasmid as the template DNA. The following oligonucleotides, and their reverse complements, were used as mutagenesis primers:

```
G291E,
                                          (SEQ ID No: 47)
5'-CTTTGAAGATTACAGATTTTGAGTTGGCGAGGGAATGGCAC-3';

R470C,
                                         (SEQ ID No.: 48)
5'-TGAGCAGCAGCTGGCAGAGTGCGAGATCGACGTGCTGGAG-3'.
```

The presence of the appropriate mutations was confirmed by DNA sequencing.

Sequences of G291E and R470C mutants of MLK4 are set forth in SEQ ID No: 49 and 50, respectively.

In the following table a list of the MLK4 mutation identified in the present study are reported with the corresponding SEQ ID No.

TABLE 3

| MLK4 mutations Amino acid level | MLK4 mutations Nucleotide level | SEQ ID No. |
|---|---|---|
| H261Y | C781T | 51 |
| H261Q | C783G | 52 |
| G291E | G872A | 49 |
| A293E | C878A | 53 |
| W296Stp | G888A | 54 |
| R470C | C1408T | 50 |
| R553Stp | C1657T | 55 |
| R555Stp | C1663T | 56 |
| N596I | A1787T | 57 |
| K629E | A1885G | 58 |
| P843S | C2788T | 59 |
| H890P | A2669C | 60 |
| M894T | T2681C | 61 |

Antibodies

MLK4 specific polyclonal antibodies were developed using a standard immunization protocol (two rabbits immunized for each epitope), we generated polyclonal antisera and antibodies directed against either the N- or the C-terminus of MLK4. Both antibodies were tested in immunoprecipitation and Western blot experiment, showing that these antibodies can be used to detect a 114 kDA protein (predicted molecular weight of MLK4) in total cell lysates. The primary antibodies used for immunoblotting were: anti-Vinculin (Sigma-Aldrich), anti-Actin (S.Cruz), anti-PERK1/2, anti-ERK1/2, anti-P-SAPK/JNK, anti-SAPK/JNK, anti-P-AKT, anti-AKT, anti-P-p38 and anti-P-38, (Cell Signaling).

Cell Culture

A-549, Colo-201 and HCT116 were cultured in RPMI-1640 medium (Invitrogen), NIH3T3, DLD-1 and HCT116-HKE-3 derived clones were grown in DMEM (Invitrogen). HTERT-HME1 were cultured in growth medium containing DMEM/F-12 (Invitrogen) supplemented with 20 ng/mL EGF, 10 ug/ml insulin, and 100 ug/ml hydrocortisone, while DiFi cells were grown in F-12 (Invitrogen). Cultures of mammalian cells were maintained in the appropriate medium supplemented with 10% fetal bovine serum (Sigma-Aldrich), 2 mM Lglutamine, 100 units/ml penicillin/streptomycin at 37° C. in humidified air with 5% $CO_2$. The mouse NIH3T3 fibroblasts are available by ATCC (CRL-1658) and were cultured in DMEM supplemented with 10% bovine serum (heat-inactivated at 56° C. for 30 min) (Invitrogen) and 2 mM L-glutamine. All the cell lines are publicly available by American Type Culture Collection (ATCC), Manassas, USA.

Transfections and Transformation Assays

NIH3T3 fibroblasts were seeded at $2\times10^5$ cells in 100 mm plate and grown for 24 h before transfection using high-efficiency liposome transfection method (Lipofectamine 2000 and Plus Reagent; Invitrogen). Each plate was transfected with 4 μg of the pCEV29.1 vector containing either no insert or a cDNA encoding for a MLK4 protein (wild-type or mutant). For co-operation experiments, cells were transiently cotransfected with 0.1 μg of RasV12 plasmid and 4 μg of pCEV containing the different MLK4 wt and mutants. Two days after transfection, cells were split into three plates cultured in DMEM containing 5% Bovine Serum and used for measuring focus formation. Foci were scored two weeks after transfection following fixation with glutharaldeyde 11% and Giemsa staining Protein Analysis Total cellular proteins were extracted by solubilizing the cells in boiling SDS buffer (50 mM Tris-HCl, pH 7.5, 150 mM NaCl, and 1% SDS). The amount of proteins was quantified by the BCA Protein Assay Reagent kit (Pierce Chemical Co.) Extracts were electrophoresed on SDS-polyacrylamide gels, transferred onto nitrocellulose membranes (Hybond; GE Healthcare) and blocked in phosphate buffered saline, 0.1% Tween 20, 5% BSA. The membrane was then incubated with appropriate dilutions of primary antibody (either MLK4, vinculin, actin, pERK, ERK, pJNK, JNK, pAKT, AKT,pP38, P38), followed by the appropriate peroxidase conjugated secondary antibody (Donkey anti Rabbit Bio-Rad Laboratories). Final detection was done by enhanced chemiluminescence (GE Healthcare). For immunoprecipitations, cells were lysed at 4° C. with 800 μl of a buffer containing 20 mM Tris-HCl [pH 7.4], 150 mM NaCl, 10% glycerol, and 1% Triton X-100 in the presence of protease and phosphatase inhibitors (1 mM $Na_3VO_4$, 100 mM NaF, 1 mM PMSF, 10 μg/ml leupeptin, 10 μg/ml aprotinin, and 1 μg/ml pepstatin). Extracts were clarified at 12,000 rpm for 20 min and quantified by bicinchoninic assay. Protein A-Sepharose beads were pre-incubated with primary antibody (1 h at +4° C.) and then washed three times with lysis buffer before incubation with total cellular proteins. Extracts were incubated with primary antibody for 2 h at +4° C. Immune complexes were collected with protein ASepharose, washed three times in lysis buffer. SDS PAGE western blotting was performed as previously described.

Ras Pull-down Assay

Cell lysates were incubated with GSTRBD on glutathioneagarose beads at 4° C. for 1 h. The beads were then collected by centrifugation, resuspended in Laemmli reducing sample buffer and boiled for 8 minutes. Western blot analysis was performed using anti-Ras antibody (Calbiochem).

Kinase Assays

Immunoprecipitated MLK4 was subjected to two independent strategies. For radioactive kinase assay, immunoprecipitates were washed three times with kinase assay buffer [50 mM Hepes (pH 7.5), 150 mM NaCl, 12.5 mM $MgCl_2$, 2 mM EGTA 1 mM dithiothreitol and 1 mM sodium orthovanadate] and the incubated with kinase buffer in the presence of 15 μM ATP including [γ-$^{32}$P]ATP for 30 min at 37° C. Reactions were stopped by the addition of 30 μl of Laemmli buffer and boiling for 1 min. Samples were analyzed by 15% SDS/PAGE followed by autoradiography.

Suppression of Gene Expression by RNAi

MLK4 expression was suppressed in tumor cells by lentiviral-mediated expression of shRNAs specifically targeting the MLK4 transcript. To rule out the variability of biological responses, we used four different shRNA directed against MLK4 sequence. ShRNA sequences were derived from the Sigma-Aldrich Mission library under accession no. NM_032435 (sequence 1, TRCN0000003209; sequence 2, TRCN0000003210; sequence 3, TRCN0000003211; sequence 4, TRCN0000003213). All sequences were able to suppress MLK4 levels while control ShCTRL (SHC002V) was not. The two most efficient ShRNA, among the different recipient cell lines, were then selected to be used in the subsequent experiments. Western blotting analysis of shRNA infected cells showed a reduction by over 80% of MLK4 protein. Results shown in the figures refer to sequence 2 and 4, renamed as Sh1 and Sh2 respectively.

Targeted Deletion of the MLK4 Locus in Human Cancer Cells

Disruption of the MLK4 exon 1 in the CRC HCT116 cells was performed as previously described (12). The targeting vector pAAV-Neo-MLK4 was constructed by PCR; DLD1 genomic was used as template for both homology arms. Constructs and primer sequences are publicly available at Università degli Studi di Torino—Dipartimento Scienze Oncologiche, strada Provinciale 142, Candiolo (TO). Clones were selected after 2 weeks of growth under 0.4 mg/ml for HCT116 cells geneticin (Invitrogen, Carlsbad, Calif.) selection and then propagated in the absence of selective agents. Homologous recombination events were identified by locus-specific PCR screening.

Anchorage-independent Growth Assays

Cells were diluted to a concentration of 500-1000 cells/ml in appropriate medium containing 5% FBS, 0.5% Seaplaque agar. Cells were seeded in 24-well plates (1 ml/well) containing a 1% agar underlay and supplemented three times a week with corresponding medium. Colonies were photographed and scored two weeks after seeding.

Invasion Assays

Cell migration and invasion assays were performed using Costar 24-well plate transwell either 8 μm pore size transwell migration plates or Matrigel matrix-coated polycarbonate filters, respectively. Lower wells containing 500 μl of media to which either 5% serum (to measure basal condition) or 10 ng/ml HGF (to measure induced invasion) had been added, whereas upper wells contained 100 μl of cells, suspended to a concentration of $10^5$ for HCT 116 or $5\times10^4$ for A549 and DLD1, in media containing the same serum concentration of lower wells. After incubation for 20 hr, cells/media in the upper wells were discarded, and the migrated cells on the underside of the transwell membranes were fixed with glutaraldeide 11% in PBS, stained with Crystal Violet and counted with Metamorph Image Analysis Software.

Drug Viability Assay

Cetuximab was obtained from the Hospital Pharmacy. Cell lines were seeded in 100 ul medium at appropriate density in 96-well plastic culture plates. Plates were incubated at 37° C. in 5% $CO_2$ for 72 h, after which cell viability was assessed by ATP content using the CellTiter-Glo® Luminescent Assay (Promega). Luminescence was detected using a DTX-880 plate reader (Beckman-Coulter).

Animal Studies

All animal procedures were approved by the Ethical Commission of the University of Turin and by the Italian Ministry of Health. Six-week-old immunocompromised CD1-/- nude athymic female mice (Charles River Laboratories, Lecco, Italy) were injected subcutaneously in right posterior flanks Tumor appearance was evacuate every 2d using a caliper. Tumor volume was calculated using the formula $V=4/3\times(d/2)2\times(D/2)$, where d is the minor tumor axis and D is the major tumor axis. Superficial pulmonary metastases were contrasted by black India ink air way infusion before excision, and were counted on dissected lung lobes under a stereoscopic microscope.

Cell lines were seeded in 100 μl medium at appropriate density in 96-well plastic culture plates. Plates were incubated with cetuximab (Erbitux) at 37° C. in 5% $CO_2$ for 72 h, after which cell viability was assessed by ATP content using the CellTiter-Glo® Luminescent Assay (Promega). Luminescence was detected using a DTX-880 plate reader (Beckman-Coulter).

Bibliography

1. A. Bardelli et al., *Science* (New York, N.Y. 300, 949 (May 9, 2003).
2. H. Davies et al., *Nature* 417, 949 (Jun. 27, 2002).
3. T. Maeda et al., *Nature* 433, 278 (Jan. 20, 2005).
4. S. Shirasawa, M. Furuse, N. Yokoyama, T. Sasazuki, *Science* (New York, N.Y. 260, 85 (Apr. 2, 1993).
5. P. M. Comoglio, L. Trusolino, *The Journal of clinical investigation* 109, 857 (April, 2002).
6. S. Velho et al., *Human molecular genetics* 19, 697 (February, 15).
7. D. Brancho et al., *Molecular and cellular biology* 25, 3670 (May, 2005).
8. S. Arena, A. Pisacane, M. Mazzone, P. M. Comoglio, A. Bardelli, *Proceedings of the National Academy of Sciences of the United States of America* 104, 11412 (Jul. 3, 2007).
9. Y. Samuels et al., *Cancer cell* 7, 561 (Jun. 2005).
10. P. Michieli et al., *Oncogene* 12, 775 (Feb. 15, 1996).
11. A. Follenzi, L. E. Ailles, S. Bakovic, M. Geuna, L. Naldini, *Nature genetics* 25, 217 (June, 2000).
12. M. Kohli, C. Rago, C. Lengauer, K. W. Kinzler, B. Vogelstein, *Nucleic acids research* 32, e3 (2004).

The invention claimed is:

1. An in vitro diagnostic method for determining the invasive potential of a tumor comprising measuring MLK4 gene expression in a tumor cell sample material of a patient;

measuring at least one activating KRAS gene mutation in said tumor cell sample material; and wherein an increased MLK4 gene expression as compared to normal level of MLK4 gene expression, and the presence of at least one activating KRAS gene mutation, indicates that the tumor is invasive.

2. The in vitro diagnostic method according to claim 1, wherein said measuring MLK4 gene expression comprises measuring MLK4 protein expression or MLK4 coding nucleic acid expression.

3. The in vitro diagnostic method according to claim 1, wherein said tumor cell sample material is a bioptic sample.

4. The in vitro diagnostic method according to claim 1, wherein said measuring MLK4 gene expression comprises measuring mutated MLK4gene expression.

5. The in vitro diagnostic method according to claim 4, wherein said mutated MLK4 gene contains at least one somatic mutation at the amino acid level selected from H261Y, H261Q, G291E, A293E, W296Stp, R470C, R553Stp, R555Stp, N5961, K629E, P843S, H890P, and M894T mutations.

6. The in vitro diagnostic method according to claim 4, wherein said mutated MLK4 gene contains at least one somatic mutation at the nucleic acid level selected from C781T, C783G, G872A, C878A, G888A, C1408T, C1657T, C1663T, A1787T, A1885G, C2788T, A2669C, T2681C mutation.

7. The in vitro diagnostic method according to claim 4, wherein measuring mutated MLK4 gene overexpression indicates that said patient will be nonresponsive to treatment with EGFR specific binding agents, including EGFR specific antibodies.

8. The in vitro diagnostic method according to claim 1, wherein said measuring MLK4 gene expression is performed using a reagent able to selectively bind to MLK4 protein and/or MLK4 coding nucleic acid and wherein said reagent is directly or indirectly labeled with a detectable substance.

9. The in vitro diagnostic method according to claim 8, wherein said reagent is an antibody specific for MLK4 protein and/or portions thereof or a nucleic acid probe specific for MLK4 nucleic acid and/or fragments thereof.

10. The in vitro diagnostic method according to claim 1, wherein said tumor is a colorectal, bladder, breast, gastric, melanoma, lung, ovary or GBM tumor.

* * * * *

SEQUENCE LISTING

```
<160> NUMBER OF SEQ ID NOS: 61

<210> SEQ ID NO 1
<211> LENGTH: 19
<212> TYPE: DNA
<213> ORGANISM: artificial
<220> FEATURE:
<223> OTHER INFORMATION: forward primer exon 1_1
```

```
<400> SEQUENCE: 1

caccgatcgc gattcctac                                                    19


<210> SEQ ID NO 2
<211> LENGTH: 18
<212> TYPE: DNA
<213> ORGANISM: artificial
<220> FEATURE:
<223> OTHER INFORMATION: reverse primer exon 1_1

<400> SEQUENCE: 2

tcgaaggcga cgtgtacc                                                     18


<210> SEQ ID NO 3
<211> LENGTH: 18
<212> TYPE: DNA
<213> ORGANISM: artificial
<220> FEATURE:
<223> OTHER INFORMATION: sequence primer exon 1_1

<400> SEQUENCE: 3

tcctaccccc tcgccttc                                                     18


<210> SEQ ID NO 4
<211> LENGTH: 18
<212> TYPE: DNA
<213> ORGANISM: artificial
<220> FEATURE:
<223> OTHER INFORMATION: forward primer exon 1_2

<400> SEQUENCE: 4

ctcagcgtcc tcgtcgtc                                                     18


<210> SEQ ID NO 5
<211> LENGTH: 18
<212> TYPE: DNA
<213> ORGANISM: artificial
<220> FEATURE:
<223> OTHER INFORMATION: reverse primer exon 1_2

<400> SEQUENCE: 5

cgcagctcga tgatgttg                                                     18


<210> SEQ ID NO 6
<211> LENGTH: 18
<212> TYPE: DNA
<213> ORGANISM: artificial
<220> FEATURE:
<223> OTHER INFORMATION: sequence primer exon 1_2

<400> SEQUENCE: 6

gcagctcgat gatgttgg                                                     18


<210> SEQ ID NO 7
<211> LENGTH: 19
<212> TYPE: DNA
<213> ORGANISM: artificial
<220> FEATURE:
<223> OTHER INFORMATION: forward primer exon 1_3

<400> SEQUENCE: 7

catcttcccc gccaactac                                                    19


<210> SEQ ID NO 8
<211> LENGTH: 18
```

<212> TYPE: DNA
<213> ORGANISM: artificial
<220> FEATURE:
<223> OTHER INFORMATION: reverse primer exon 1_3

<400> SEQUENCE: 8
ggcccagttg accagcac 18

<210> SEQ ID NO 9
<211> LENGTH: 18
<212> TYPE: DNA
<213> ORGANISM: artificial
<220> FEATURE:
<223> OTHER INFORMATION: sequence primer exon 1_3

<400> SEQUENCE: 9
tcttccccgc caactacg 18

<210> SEQ ID NO 10
<211> LENGTH: 18
<212> TYPE: DNA
<213> ORGANISM: artificial
<220> FEATURE:
<223> OTHER INFORMATION: forward primer exon 1_4

<400> SEQUENCE: 10
caggaggtgg ccgtgaag 18

<210> SEQ ID NO 11
<211> LENGTH: 18
<212> TYPE: DNA
<213> ORGANISM: artificial
<220> FEATURE:
<223> OTHER INFORMATION: reverse primer exon 1_4

<400> SEQUENCE: 11
cgccctaagg ctgactcc 18

<210> SEQ ID NO 12
<211> LENGTH: 20
<212> TYPE: DNA
<213> ORGANISM: artificial
<220> FEATURE:
<223> OTHER INFORMATION: sequence primer exon 1_4

<400> SEQUENCE: 12
ctcccacctc tttccatctg 20

<210> SEQ ID NO 13
<211> LENGTH: 18
<212> TYPE: DNA
<213> ORGANISM: artificial
<220> FEATURE:
<223> OTHER INFORMATION: forward primer exon 1_5

<400> SEQUENCE: 13
gcacgtgctg gtcaactg 18

<210> SEQ ID NO 14
<211> LENGTH: 18
<212> TYPE: DNA
<213> ORGANISM: artificial
<220> FEATURE:
<223> OTHER INFORMATION: reverse primer exon 1_5

<400> SEQUENCE: 14
cgccctaagg ctgactcc 18

<210> SEQ ID NO 15
<211> LENGTH: 18
<212> TYPE: DNA
<213> ORGANISM: artificial
<220> FEATURE:
<223> OTHER INFORMATION: sequence primer exon 1_5

<400> SEQUENCE: 15
actgggccgt gcagatag 18

<210> SEQ ID NO 16
<211> LENGTH: 23
<212> TYPE: DNA
<213> ORGANISM: artificial
<220> FEATURE:
<223> OTHER INFORMATION: forward primer exon 2

<400> SEQUENCE: 16
caggcacaga taacccacta aag 23

<210> SEQ ID NO 17
<211> LENGTH: 26
<212> TYPE: DNA
<213> ORGANISM: artificial
<220> FEATURE:
<223> OTHER INFORMATION: reverse primer exon 2

<400> SEQUENCE: 17
aaaccataaa aattcattca aaaagg 26

<210> SEQ ID NO 18
<211> LENGTH: 20
<212> TYPE: DNA
<213> ORGANISM: artificial
<220> FEATURE:
<223> OTHER INFORMATION: sequence primer exon 2

<400> SEQUENCE: 18
catgccacag aaaaattgtg 20

<210> SEQ ID NO 19
<211> LENGTH: 21
<212> TYPE: DNA
<213> ORGANISM: artificial
<220> FEATURE:
<223> OTHER INFORMATION: forward primer exon 5

<400> SEQUENCE: 19
gggaatttca gcttctcctt g 21

<210> SEQ ID NO 20
<211> LENGTH: 22
<212> TYPE: DNA
<213> ORGANISM: artificial
<220> FEATURE:
<223> OTHER INFORMATION: reverse primer exon 5

<400> SEQUENCE: 20
ccctatctct ttcctggttc tg 22

<210> SEQ ID NO 21
<211> LENGTH: 18
<212> TYPE: DNA
<213> ORGANISM: artificial

<220> FEATURE:
<223> OTHER INFORMATION: sequence primer exon 5

<400> SEQUENCE: 21
ggggtcgcca gtgtagtg 18

<210> SEQ ID NO 22
<211> LENGTH: 21
<212> TYPE: DNA
<213> ORGANISM: artificial
<220> FEATURE:
<223> OTHER INFORMATION: forward primer exon 6_1

<400> SEQUENCE: 22
cgatcctgca atattctttg c 21

<210> SEQ ID NO 23
<211> LENGTH: 20
<212> TYPE: DNA
<213> ORGANISM: artificial
<220> FEATURE:
<223> OTHER INFORMATION: reverse primer exon 6_1

<400> SEQUENCE: 23
gtggcaccta cgaaatgtcc 20

<210> SEQ ID NO 24
<211> LENGTH: 22
<212> TYPE: DNA
<213> ORGANISM: artificial
<220> FEATURE:
<223> OTHER INFORMATION: sequence primer exon 6_1

<400> SEQUENCE: 24
ttgctgtgtg ctaaatacat gg 22

<210> SEQ ID NO 25
<211> LENGTH: 25
<212> TYPE: DNA
<213> ORGANISM: artificial
<220> FEATURE:
<223> OTHER INFORMATION: forward primer exon 7_2

<400> SEQUENCE: 25
tttctcattg ttttcatgtt ttgag 25

<210> SEQ ID NO 26
<211> LENGTH: 27
<212> TYPE: DNA
<213> ORGANISM: artificial
<220> FEATURE:
<223> OTHER INFORMATION: reverse primer exon 7_2

<400> SEQUENCE: 26
gcatgataaa ttcatcctag aaaattg 27

<210> SEQ ID NO 27
<211> LENGTH: 26
<212> TYPE: DNA
<213> ORGANISM: artificial
<220> FEATURE:
<223> OTHER INFORMATION: sequence primer exon 7_2

<400> SEQUENCE: 27
ttttgagtaa ggtagtttca caactg 26

<210> SEQ ID NO 28
<211> LENGTH: 20
<212> TYPE: DNA
<213> ORGANISM: artificial
<220> FEATURE:
<223> OTHER INFORMATION: forward primer exon 8

<400> SEQUENCE: 28
ttgtcagccc ttcaaaactg 20

<210> SEQ ID NO 29
<211> LENGTH: 20
<212> TYPE: DNA
<213> ORGANISM: artificial
<220> FEATURE:
<223> OTHER INFORMATION: reverse primer exon 8

<400> SEQUENCE: 29
cttgctaatc tcccctctgc 20

<210> SEQ ID NO 30
<211> LENGTH: 21
<212> TYPE: DNA
<213> ORGANISM: artificial
<220> FEATURE:
<223> OTHER INFORMATION: sequence primer exon 8

<400> SEQUENCE: 30
tggtctgtat ccaccaaaac c 21

<210> SEQ ID NO 31
<211> LENGTH: 37
<212> TYPE: DNA
<213> ORGANISM: artificial
<220> FEATURE:
<223> OTHER INFORMATION: forward primer exon 9_1

<400> SEQUENCE: 31
gtaaaacgac ggccagtgaa aagggctgca tgtgttt 37

<210> SEQ ID NO 32
<211> LENGTH: 21
<212> TYPE: DNA
<213> ORGANISM: artificial
<220> FEATURE:
<223> OTHER INFORMATION: reverse primer exon 9_1

<400> SEQUENCE: 32
ctctctgagc atctttccca a 21

<210> SEQ ID NO 33
<211> LENGTH: 17
<212> TYPE: DNA
<213> ORGANISM: artificial
<220> FEATURE:
<223> OTHER INFORMATION: sequence primer exon 9_1

<400> SEQUENCE: 33
gtaaaacgac ggccagt 17

<210> SEQ ID NO 34
<211> LENGTH: 23
<212> TYPE: DNA
<213> ORGANISM: artificial
<220> FEATURE:
<223> OTHER INFORMATION: forward primer exon 9_2

<400> SEQUENCE: 34
gcctacattg atctacctct tgg 23

<210> SEQ ID NO 35
<211> LENGTH: 37
<212> TYPE: DNA
<213> ORGANISM: artificial
<220> FEATURE:
<223> OTHER INFORMATION: reverse primer exon 9_2

<400> SEQUENCE: 35
gtaaaacgac ggccagttct tctcttcctt gggcaac 37

<210> SEQ ID NO 36
<211> LENGTH: 17
<212> TYPE: DNA
<213> ORGANISM: artificial
<220> FEATURE:
<223> OTHER INFORMATION: sequence primer exon 9_2

<400> SEQUENCE: 36
gtaaaacgac ggccagt 17

<210> SEQ ID NO 37
<211> LENGTH: 20
<212> TYPE: DNA
<213> ORGANISM: artificial
<220> FEATURE:
<223> OTHER INFORMATION: forward primer exon 9_3

<400> SEQUENCE: 37
cataaagcac aggctgctga 20

<210> SEQ ID NO 38
<211> LENGTH: 37
<212> TYPE: DNA
<213> ORGANISM: artificial
<220> FEATURE:
<223> OTHER INFORMATION: reverse primer exon 9_3

<400> SEQUENCE: 38
gtaaaacgac ggccagtagc aggcactttg tggagaa 37

<210> SEQ ID NO 39
<211> LENGTH: 17
<212> TYPE: DNA
<213> ORGANISM: artificial
<220> FEATURE:
<223> OTHER INFORMATION: sequence primer exon 9_3

<400> SEQUENCE: 39
gtaaaacgac ggccagt 17

<210> SEQ ID NO 40
<211> LENGTH: 38
<212> TYPE: DNA
<213> ORGANISM: artificial
<220> FEATURE:
<223> OTHER INFORMATION: forward primer exon 9_4

<400> SEQUENCE: 40
gtaaaacgac ggccagtcca caccttcttt ctccacaa 38

<210> SEQ ID NO 41

```
<211> LENGTH: 20
<212> TYPE: DNA
<213> ORGANISM: artificial
<220> FEATURE:
<223> OTHER INFORMATION: reverse primer exon 9_4

<400> SEQUENCE: 41

cattcccaca tgtctgctgt                                                  20


<210> SEQ ID NO 42
<211> LENGTH: 17
<212> TYPE: DNA
<213> ORGANISM: artificial
<220> FEATURE:
<223> OTHER INFORMATION: sequence primer exon 9_4

<400> SEQUENCE: 42

gtaaaacgac ggccagt                                                     17


<210> SEQ ID NO 43
<211> LENGTH: 37
<212> TYPE: DNA
<213> ORGANISM: artificial
<220> FEATURE:
<223> OTHER INFORMATION: forward primer exon 9_5

<400> SEQUENCE: 43

gtaaaacgac ggccagtcaa gaaacttgcc gtcttcc                               37


<210> SEQ ID NO 44
<211> LENGTH: 26
<212> TYPE: DNA
<213> ORGANISM: artificial
<220> FEATURE:
<223> OTHER INFORMATION: reverse primer exon 9_5

<400> SEQUENCE: 44

caaattatta aatgtcatca ccagga                                           26


<210> SEQ ID NO 45
<211> LENGTH: 17
<212> TYPE: DNA
<213> ORGANISM: artificial
<220> FEATURE:
<223> OTHER INFORMATION: sequence primer exon 9_5

<400> SEQUENCE: 45

gtaaaacgac ggccagt                                                     17


<210> SEQ ID NO 46
<211> LENGTH: 3111
<212> TYPE: DNA
<213> ORGANISM: homo sapiens

<400> SEQUENCE: 46

atggctttgc ggggcgccgc gggagcgacc gacaccccgg tgtcctcggc cgggggagcc      60

cccggcggct cagcgtcctc gtcgtccacc tcctcgggcg gctcggcctc ggcgggcgcg     120

gggctgtggg ccgcgctcta tgactacgag gctcgcggcg aggacgagct gagcctgcgg     180

cgcggccagc tggtggaggt gctgtcgcag gacgccgccg tgtcgggcga cgagggctgg     240

tgggcaggcc aggtgcagcg gcgcctcggc atcttccccg ccaactacgt ggctccctgc     300

cgcccggccg ccagccccgc gccgccgccc tcgcggccca gctccccggt acacgtcgcc     360

ttcgagcggc tggagctgaa ggagctcatc ggcgctgggg gcttcgggca ggtgtaccgc     420
```

```
gccacctggc agggccagga ggtggccgtg aaggcggcgc gccaggaccc ggagcaggac    480
gcggcggcgg ctgccgagag cgtgcggcgc gaggctcggc tcttcgccat gctgcggcac    540
cccaacatca tcgagctgcg cggcgtgtgc ctgcagcagc cgcacctctg cctggtgctg    600
gagttcgccc gcggcggagc gctcaaccga gcgctggccg ctgccaacgc cgccccggac    660
ccgcgcgcgc ccggcccccg ccgcgcgcgc cgcatccctc cgcacgtgct ggtcaactgg    720
gccgtgcaga tagcgcgggg catgctctac ctgcatgagg aggccttcgt gcccatcctg    780
caccgggacc tcaagtccag caacattttg ctacttgaga agatagaaca tgatgacatc    840
tgcaataaaa ctttgaagat tacagatttt gggttggcga gggaatggca caggaccacc    900
aaaatgagca cagcaggcac ctatgcctgg atggcccccg aagtgatcaa gtcttccttg    960
ttttctaagg gaagcgacat ctggagctat ggagtgctgc tgtgggaact gctcaccgga   1020
gaagtcccct atcggggcat tgatggcctc gccgtggctt atggggtagc agtcaataaa   1080
ctcactttgc ccattccatc cacctgccct gagccgtttg ccaagctcat gaaagaatgc   1140
tggcaacaag accctcatat tcgtccatcg tttgccttaa ttctcgaaca gttgactgct   1200
attgaagggg cagtgatgac tgagatgcct caagaatctt ttcattccat gcaagatgac   1260
tggaaactag aaattcaaca aatgtttgat gagttgagaa caaaggaaaa ggagctgcga   1320
tcccgggaag aggagctgac tcgggcggct ctgcagcaga agtctcagga ggagctgcta   1380
aagcggcgtg agcagcagct ggcagagcgc gagatcgacg tgctggagcg ggaacttaac   1440
attctgatat tccagctaaa ccaggagaag cccaaggtaa agaagaggaa gggcaagttt   1500
aagagaagtc gtttaaagct caaagatgga catcgaatca gtttaccttc agatttccag   1560
cacaagataa ccgtgcaggc ctctcccaac ttggacaaac ggcggagcct gaacagcagc   1620
agttccagtc ccccgagcag ccccacaatg atgccccgac tccgagccat acagttgact   1680
tcagatgaaa gcaataaaac ttggggaagg aacacagtct ttcgacaaga agaatttgag   1740
gatgtaaaaa ggaattttaa gaaaaaaggt tgtacctggg gaccaaattc cattcaaatg   1800
aaagatagaa cagattgcaa agaaaggata agacctctct ccgatggcaa cagtccttgg   1860
tcaactatct taataaaaaa tcagaaaacc atgcccttgg cttcattgtt tgtggaccag   1920
ccagggtcct gtgaagagcc aaaactttcc cctgatggat tagaacacag aaaaccaaaa   1980
caaataaaat tgcctagtca ggcctacatt gatctacctc ttgggaaaga tgctcagaga   2040
gagaatcctg cagaagctga aagctgggag gaggcagcct ctgcgaatgc tgccacagtc   2100
tccattgaga tgactcctac gaatagtctg agtagatccc cccagagaaa gaaaacggag   2160
tcagctctgt atgggtgcac cgtccttctg gcatcggtgg ctctgggact ggacctcaga   2220
gagcttcata aagcacaggc tgctgaagaa ccgttgccca aggaagagaa gaagaaacga   2280
gagggaatct tccagcgggc ttccaagtcc cgcagaagcg ccagtcctcc cacaagcctg   2340
ccatccacct gtggggaggc cagcagccca ccctccctgc cactgtcaag tgccctgggc   2400
atcctctcca caccttcttt ctccacaaag tgcctgctgc agatggacag tgaagatcca   2460
ctggtggaca gtgcacctgt cacttgtgac tctgagatgc tcactccgga tttttgtccc   2520
actgccccag gaagtggtcg tgagccagcc ctcatgccaa gacttgacac tgattgtagt   2580
gtatcaagaa acttgccgtc ttccttccta cagcagacat gtgggaatgt accttactgt   2640
gcttcttcaa aacatagacc gtcacatcac agacggacca tgtctgatgg aaatccgacc   2700
ccaactggtg caactattat ctcagccact ggagcctctg cactgccact ctgcccctca   2760
```

```
cctgctcctc acagtcatct gccaagggag gtctcaccca agaagcacag cactgtccac   2820

atcgtgcctc agcgtcgccc tgcctccctg agaagccgct cagatctgcc tcaggcttac   2880

ccacagacag cagtgtctca gctggcacag actgcctgtg tagtgggtcg cccaggacca   2940

catcccaccc aattcctcgc tgccaaggag agaactaaat cccatgtgcc ttcattactg   3000

gatgctgacg tggaaggtca gagcagggac tacactgtgc cactgtgcag aatgaggagc   3060

aaaaccagcc ggccatctat atatgaactg gagaaagaat tcctgtctta a            3111
```

<210> SEQ ID NO 47
<211> LENGTH: 41
<212> TYPE: DNA
<213> ORGANISM: artificial
<220> FEATURE:
<223> OTHER INFORMATION: mutagenesis primer G291E

<400> SEQUENCE: 47

```
ctttgaagat tacagatttt gagttggcga gggaatggca c                         41
```

<210> SEQ ID NO 48
<211> LENGTH: 40
<212> TYPE: DNA
<213> ORGANISM: artificial
<220> FEATURE:
<223> OTHER INFORMATION: mutagenesis primer R470C

<400> SEQUENCE: 48

```
tgagcagcag ctggcagagt gcgagatcga cgtgctggag                           40
```

<210> SEQ ID NO 49
<211> LENGTH: 3041
<212> TYPE: DNA
<213> ORGANISM: homo sapiens

<400> SEQUENCE: 49

```
atggctttgc ggggcgccgc gggagcgacc gacaccccgg tgtcctcggc cgggggagcc     60

cccggcggct cagcgtcctc gtcgtccacc tcctcgggcg gctcggcctc ggcgggcgcg    120

gggctgtggg ccgcgctcta tgactacgag gctcgcggcg aggacgagct gagcctgcgg    180

cgcggccagc tggtggaggt gctgtcgcag gacgccgccg tgtcgggcga cgagggctgg    240

tgggcaggcc aggtgcagcg gcgcctcggc atcttccccg ccaactacgt ggctccctgc    300

cgcccggccg ccagccccgc gccgccgccc tcgcggccca gctccccggt acacgtcgcc    360

ttcgagcggc tggagctgaa ggagctcatc ggcgctgggg gcttcgggca ggtgtaccgc    420

gccacctggc agggccagga ggtggccgtg aaggcggcgc gccaggaccc ggagcaggac    480

gcggcggcgg ctgccgagag cgtgcggcgc gaggctcggc tcttcgccat gctgcggcac    540

cccaacatca tcgagctgcg cggcgtgtgc ctgcagcagc cgcacctctg cctggtgctg    600

gagttcgccc gcggcggagc gctcaaccga gcgctggccg ctgccaacgc cgccccggac    660

ccgcgcgcgc ccggcccccg ccgcgcgcgc cgcatccctc cgcacgtgct ggtcaactgg    720

gccgtgcaga tagcgcgggg catgctctac ctgcatgagg aggccttcgt gcccatcctg    780

caccgggacc tcaagtccag caacattttg ctacttgaga agatagaaca tgatgacatc    840

tgcaataaaa ctttgaagat tacagatttt gagttggcga gggaatggca caggaccacc    900

aaaatgagca cagcaggcac ctatgcctgg atggcccccg aagtgatcaa gtcttccttg    960

ttttctaagg gaagcgacat ctggagctat ggagtgctgc tgtgggaact gctcaccgga   1020

gaagtcccct atcggggcat tgatggcctc gccgtggctt atggggtagc agtcaataaa   1080
```

-continued

```
ctcactttgc ccattccatc cacctgccct gagccgtttg ccaagctcat gaaagaatgc   1140

tggcaacaag accctcatat tcgtccatcg tttgccttaa ttctcgaaca gttgactgct   1200

attgaagggg cagtgatgac tgagatgcct caagaatctt ttcattccat gcaagatgac   1260

tggaaactag aaattcaaca aatgtttgat gagttgagaa caaaggaaaa ggagctgcga   1320

tcccgggaag aggagctgac tcgggcggct ctgcagcaga agtctcagga ggagctgcta   1380

aagcggcgtg agcagcagct ggcagagcgc gagatcgacg tgctggagcg ggaacttaac   1440

attctgatat tccagctaaa ccaggagaag cccaaggtaa agaagaggaa gggcaagttt   1500

aagagaagtc gtttaaagct caaagatgga catcgaatca gtttaccttc agatttccag   1560

cacaagataa ccgtgcaggc ctctcccaac ttggacaaac ggcggagcct gaacagcagc   1620

agttccagtc ccccgagcag ccccacaatg atgccccgac tccgagccat acagttgact   1680

tcagatgaaa gcaataaaac ttggggaagg aacacagtct ttcgacaaga agaatttgag   1740

gatgtaaaaa ggaattttaa gaaaaaaggt tgtacctggg gaccaaattc cattcaaatg   1800

aaagatagaa cagattgcaa agaaaggata agacctctct ccgatggcaa cagtccttgg   1860

tcaactatct taataaaaaa tcagaaaacc atgcccttgg cttcattgtt tgtggaccag   1920

ccagggtcct gtgaagagcc aaaactttcc cctgatggat tagaacacag aaaaccaaaa   1980

caaataaaat tgcctagtca ggcctacatt gatctacctc ttgggaaaga tgctcagaga   2040

gagaatcctg cagaagctga aagctgggag gaggcagcct ctgcgaatgc tgccacagtc   2100

tccattgaga tgactcctac gaatagtctg agtagatccc cccagagaaa gaaaacggag   2160

tcagctctgt atgggtgcac cgtccttctg gcatcggtgg ctctgggact ggacctcaga   2220

gagcttcata aagcacaggc tgctgaagaa ccgttgccca aggaagagaa gaagaaacga   2280

gagggaatct tccagcgggc ttccaagtcc cgcagaagcg ccagtcctcc cacaagcctg   2340

ccatccacct gtggggaggc cagcagccca ccctccctgc cactgtcaag tgccctgggc   2400

atcctctcca caccttcttt ctccacaaag tgcctgctgc agatggacag tgaagatcca   2460

ctggtggaca gtgcacctgt cacttgtgac tctgagatgc tcactccgga tttttgtccc   2520

actgccccag gaagtggtcg tgagccagcc ctcatgccaa gacttgacac tgattgtagt   2580

gtatcaagaa acttgccgtc ttccttccta cagcagacat gtgggaatgt accttactgt   2640

gcttcttcaa aacatagacc gtcacatcac agacggacca tgtctgatgg aaatccgacc   2700

ccaactggtg caactattat ctcagccact ggagcctctg cactgccact ctgcccctca   2760

cctgctcctc acagtcatct gccaagggag gtctcaccca agaagcacag cactgtccac   2820

atcgtgcctc agcgtcgccc tgcctccctg agaagccgct cagatctgcc tcaggcttac   2880

ccacagacag cagtgtctca gctggcacag actgcctgtg tagtgggtcg cccaggacca   2940

catcccaccc aattcctcgc tgccaaggag agaactaaat cccatgtgcc ttcattactg   3000

gatgctgacg tggaaggtca gagcagggac tacactgtgc c                       3041
```

<210> SEQ ID NO 50
<211> LENGTH: 3041
<212> TYPE: DNA
<213> ORGANISM: homo sapiens

<400> SEQUENCE: 50

```
atggctttgc ggggcgccgc gggagcgacc gacaccccgg tgtcctcggc cgggggagcc     60

cccggcggct cagcgtcctc gtcgtccacc tcctcgggcg gctcggcctc ggcgggcgcg    120
```

-continued

```
gggctgtggg ccgcgctcta tgactacgag gctcgcggcg aggacgagct gagcctgcgg    180
cgcggccagc tggtggaggt gctgtcgcag gacgccgccg tgtcgggcga cgagggctgg    240
tgggcaggcc aggtgcagcg gcgcctcggc atcttccccg ccaactacgt ggctccctgc    300
cgcccggccg ccagccccgc gccgccgccc tcgcggccca gctccccggt acacgtcgcc    360
ttcgagcggc tggagctgaa ggagctcatc ggcgctgggg gcttcgggca ggtgtaccgc    420
gccacctggc agggccagga ggtggccgtg aaggcggcgc gccaggaccc ggagcaggac    480
gcggcggcgg ctgccgagag cgtgcggcgc gaggctcggc tcttcgccat gctgcggcac    540
cccaacatca tcgagctgcg cggcgtgtgc ctgcagcagc cgcacctctg cctggtgctg    600
gagttcgccc gcggcggagc gctcaaccga gcgctggccg ctgccaacgc cgccccggac    660
ccgcgcgcgc ccggcccccg ccgcgcgcgc cgcatccctc cgcacgtgct ggtcaactgg    720
gccgtgcaga tagcgcgggg catgctctac ctgcatgagg aggccttcgt gcccatcctg    780
caccgggacc tcaagtccag caacattttg ctacttgaga agatagaaca tgatgacatc    840
tgcaataaaa ctttgaagat tacagatttt gggttggcga gggaatggca caggaccacc    900
aaaatgagca cagcaggcac ctatgcctgg atggcccccg aagtgatcaa gtcttccttg    960
ttttctaagg gaagcgacat ctggagctat ggagtgctgc tgtgggaact gctcaccgga   1020
gaagtcccct atcggggcat tgatggcctc gccgtggctt atggggtagc agtcaataaa   1080
ctcactttgc ccattccatc cacctgccct gagccgtttg ccaagctcat gaaagaatgc   1140
tggcaacaag accctcatat tcgtccatcg tttgccttaa ttctcgaaca gttgactgct   1200
attgaagggg cagtgatgac tgagatgcct caagaatctt ttcattccat gcaagatgac   1260
tggaaactag aaattcaaca aatgtttgat gagttgagaa caaaggaaaa ggagctgcga   1320
tcccgggaag aggagctgac tcgggcggct ctgcagcaga agtctcagga ggagctgcta   1380
aagcggcgtg agcagcagct ggcagagtgc gagatcgacg tgctggagcg ggaacttaac   1440
attctgatat tccagctaaa ccaggagaag cccaaggtaa agaagaggaa gggcaagttt   1500
aagagaagtc gtttaaagct caaagatgga catcgaatca gtttaccttc agatttccag   1560
cacaagataa ccgtgcaggc ctctcccaac ttggacaaac ggcggagcct gaacagcagc   1620
agttccagtc ccccgagcag ccccacaatg atgccccgac tccgagccat acagttgact   1680
tcagatgaaa gcaataaaac ttggggaagg aacacagtct ttcgacaaga agaatttgag   1740
gatgtaaaaa ggaattttaa gaaaaaaggt tgtacctggg gaccaaattc cattcaaatg   1800
aaagatagaa cagattgcaa agaaaggata agacctctct ccgatggcaa cagtccttgg   1860
tcaactatct taataaaaaa tcagaaaacc atgcccttgg cttcattgtt tgtggaccag   1920
ccagggtcct gtgaagagcc aaaactttcc cctgatggat tagaacacag aaaaccaaaa   1980
caaataaaat tgcctagtca ggcctacatt gatctacctc ttgggaaaga tgctcagaga   2040
gagaatcctg cagaagctga aagctgggag gaggcagcct ctgcgaatgc tgccacagtc   2100
tccattgaga tgactcctac gaatagtctg agtagatccc cccagagaaa gaaaacggag   2160
tcagctctgt atgggtgcac cgtccttctg gcatcggtgg ctctgggact ggacctcaga   2220
gagcttcata aagcacaggc tgctgaagaa ccgttgccca aggaagagaa gaagaaacga   2280
gagggaatct tccagcgggc ttccaagtcc cgcagaagcg ccagtcctcc cacaagcctg   2340
ccatccacct gtggggaggc cagcagccca ccctccctgc cactgtcaag tgccctgggc   2400
atcctctcca caccttcttt ctccacaaag tgcctgctgc agatggacag tgaagatcca   2460
ctggtggaca gtgcacctgt cacttgtgac tctgagatgc tcactccgga tttttgtccc   2520
```

```
actgccccag gaagtggtcg tgagccagcc ctcatgccaa gacttgacac tgattgtagt   2580

gtatcaagaa acttgccgtc ttccttccta cagcagacat gtgggaatgt accttactgt   2640

gcttcttcaa aacatagacc gtcacatcac agacggacca tgtctgatgg aaatccgacc   2700

ccaactggtg caactattat ctcagccact ggagcctctg cactgccact ctgcccctca   2760

cctgctcctc acagtcatct gccaagggag gtctcaccca agaagcacag cactgtccac   2820

atcgtgcctc agcgtcgccc tgcctccctg agaagccgct cagatctgcc tcaggcttac   2880

ccacagacag cagtgtctca gctggcacag actgcctgtg tagtgggtcg cccaggacca   2940

catcccaccc aattcctcgc tgccaaggag agaactaaat cccatgtgcc ttcattactg   3000

gatgctgacg tggaaggtca gagcagggac tacactgtgc c                         3041
```

```
<210> SEQ ID NO 51
<211> LENGTH: 3041
<212> TYPE: DNA
<213> ORGANISM: homo sapiens

<400> SEQUENCE: 51
```

```
atggctttgc ggggcgccgc gggagcgacc gacaccccgg tgtcctcggc cgggggagcc     60

cccggcggct cagcgtcctc gtcgtccacc tcctcgggcg gctcggcctc ggcgggcgcg    120

gggctgtggg ccgcgctcta tgactacgag gctcgcggcg aggacgagct gagcctgcgg    180

cgcggccagc tggtggaggt gctgtcgcag gacgccgccg tgtcgggcga cgagggctgg    240

tgggcaggcc aggtgcagcg gcgcctcggc atcttccccg ccaactacgt ggctccctgc    300

cgcccggccg ccagccccgc gccgccgccc tcgcggccca gctccccggt acacgtcgcc    360

ttcgagcggc tggagctgaa ggagctcatc ggcgctgggg gcttcgggca ggtgtaccgc    420

gccacctggc agggccagga ggtggccgtg aaggcggcgc gccaggaccc ggagcaggac    480

gcggcggcgg ctgccgagag cgtgcggcgc gaggctcggc tcttcgccat gctgcggcac    540

cccaacatca tcgagctgcg cggcgtgtgc ctgcagcagc cgcacctctg cctggtgctg    600

gagttcgccc gcggcggagc gctcaaccga gcgctggccg ctgccaacgc cgccccggac    660

ccgcgcgcgc ccggcccccg ccgcgcgcgc cgcatccctc cgcacgtgct ggtcaactgg    720

gccgtgcaga tagcgcgggg catgctctac ctgcatgagg aggccttcgt gcccatcctg    780

taccgggacc tcaagtccag caacattttg ctacttgaga agatagaaca tgatgacatc    840

tgcaataaaa ctttgaagat tacagatttt gggttggcga gggaatggca caggaccacc    900

aaaatgagca cagcaggcac ctatgcctgg atggcccccg aagtgatcaa gtcttccttg    960

ttttctaagg gaagcgacat ctggagctat ggagtgctgc tgtgggaact gctcaccgga   1020

gaagtcccct atcggggcat tgatggcctc gccgtggctt atggggtagc agtcaataaa   1080

ctcactttgc ccattccatc cacctgccct gagccgtttg ccaagctcat gaaagaatgc   1140

tggcaacaag accctcatat tcgtccatcg tttgccttaa ttctcgaaca gttgactgct   1200

attgaagggg cagtgatgac tgagatgcct caagaatctt ttcattccat gcaagatgac   1260

tggaaactag aaattcaaca aatgtttgat gagttgagaa caaaggaaaa ggagctgcga   1320

tcccgggaag aggagctgac tcgggcggct ctgcagcaga agtctcagga ggagctgcta   1380

aagcggcgtg agcagcagct ggcagagcgc gagatcgacg tgctggagcg ggaacttaac   1440

attctgatat tccagctaaa ccaggagaag cccaaggtaa agaagaggaa gggcaagttt   1500

aagagaagtc gtttaaagct caaagatgga catcgaatca gtttaccttc agatttccag   1560
```

```
cacaagataa ccgtgcaggc ctctcccaac ttggacaaac ggcggagcct gaacagcagc   1620

agttccagtc ccccgagcag ccccacaatg atgccccgac tccgagccat acagttgact   1680

tcagatgaaa gcaataaaac ttggggaagg aacacagtct ttcgacaaga agaatttgag   1740

gatgtaaaaa ggaattttaa gaaaaaaggt tgtacctggg gaccaaattc cattcaaatg   1800

aaagatagaa cagattgcaa agaaaggata agacctctct ccgatggcaa cagtccttgg   1860

tcaactatct taataaaaaa tcagaaaacc atgcccttgg cttcattgtt tgtggaccag   1920

ccagggtcct gtgaagagcc aaaactttcc cctgatggat tagaacacag aaaaccaaaa   1980

caaataaaat tgcctagtca ggcctacatt gatctacctc ttgggaaaga tgctcagaga   2040

gagaatcctg cagaagctga aagctgggag gaggcagcct ctgcgaatgc tgccacagtc   2100

tccattgaga tgactcctac gaatagtctg agtagatccc cccagagaaa gaaaacggag   2160

tcagctctgt atgggtgcac cgtccttctg gcatcggtgg ctctgggact ggacctcaga   2220

gagcttcata aagcacaggc tgctgaagaa ccgttgccca aggaagagaa gaagaaacga   2280

gagggaatct tccagcgggc ttccaagtcc cgcagaagcg ccagtcctcc cacaagcctg   2340

ccatccacct gtggggaggc cagcagccca ccctccctgc cactgtcaag tgccctgggc   2400

atcctctcca caccttcttt ctccacaaag tgcctgctgc agatggacag tgaagatcca   2460

ctggtggaca gtgcacctgt cacttgtgac tctgagatgc tcactccgga tttttgtccc   2520

actgccccag gaagtggtcg tgagccagcc ctcatgccaa gacttgacac tgattgtagt   2580

gtatcaagaa acttgccgtc ttccttccta cagcagacat gtgggaatgt accttactgt   2640

gcttcttcaa aacatagacc gtcacatcac agacggacca tgtctgatgg aaatccgacc   2700

ccaactggtg caactattat ctcagccact ggagcctctg cactgccact ctgcccctca   2760

cctgctcctc acagtcatct gccaagggag gtctcaccca agaagcacag cactgtccac   2820

atcgtgcctc agcgtcgccc tgcctccctg agaagccgct cagatctgcc tcaggcttac   2880

ccacagacag cagtgtctca gctggcacag actgcctgtg tagtgggtcg cccaggacca   2940

catcccaccc aattcctcgc tgccaaggag agaactaaat cccatgtgcc ttcattactg   3000

gatgctgacg tggaaggtca gagcagggac tacactgtgc c                        3041
```

<210> SEQ ID NO 52
<211> LENGTH: 3041
<212> TYPE: DNA
<213> ORGANISM: homo sapiens

<400> SEQUENCE: 52

```
atggctttgc ggggcgccgc gggagcgacc gacaccccgg tgtcctcggc cgggggagcc     60

cccggcggct cagcgtcctc gtcgtccacc tcctcgggcg gctcggcctc ggcgggcgcg    120

gggctgtggg ccgcgctcta tgactacgag gctcgcggcg aggacgagct gagcctgcgg    180

cgcggccagc tggtggaggt gctgtcgcag gacgccgccg tgtcgggcga cgagggctgg    240

tgggcaggcc aggtgcagcg gcgcctcggc atcttccccg ccaactacgt ggctccctgc    300

cgcccggccg ccagccccgc gccgccgccc tcgcggccca gctccccggt acacgtcgcc    360

ttcgagcggc tggagctgaa ggagctcatc ggcgctgggg gcttcgggca ggtgtaccgc    420

gccacctggc agggccagga ggtggccgtg aaggcggcgc gccaggaccc ggagcaggac    480

gcggcggcgg ctgccgagag cgtgcggcgc gaggctcggc tcttcgccat gctgcggcac    540

cccaacatca tcgagctgcg cggcgtgtgc ctgcagcagc cgcacctctg cctggtgctg    600

gagttcgccc gcggcggagc gctcaaccga gcgctggccg ctgccaacgc cgccccggac    660
```

-continued

```
ccgcgcgcgc ccggcccccg ccgcgcgcgc cgcatccctc cgcacgtgct ggtcaactgg    720
gccgtgcaga tagcgcgggg catgctctac ctgcatgagg aggccttcgt gcccatcctg    780
cagcgggacc tcaagtccag caacattttg ctacttgaga agatagaaca tgatgacatc    840
tgcaataaaa ctttgaagat tacagatttt gggttggcga gggaatggca caggaccacc    900
aaaatgagca cagcaggcac ctatgcctgg atggcccccg aagtgatcaa gtcttccttg    960
ttttctaagg gaagcgacat ctggagctat ggagtgctgc tgtgggaact gctcaccgga   1020
gaagtcccct atcggggcat tgatggcctc gccgtggctt atggggtagc agtcaataaa   1080
ctcactttgc ccattccatc cacctgccct gagccgtttg ccaagctcat gaaagaatgc   1140
tggcaacaag accctcatat tcgtccatcg tttgccttaa ttctcgaaca gttgactgct   1200
attgaagggg cagtgatgac tgagatgcct caagaatctt ttcattccat gcaagatgac   1260
tggaaactag aaattcaaca aatgtttgat gagttgagaa caaaggaaaa ggagctgcga   1320
tcccgggaag aggagctgac tcgggcggct ctgcagcaga agtctcagga ggagctgcta   1380
aagcggcgtg agcagcagct ggcagagcgc gagatcgacg tgctggagcg ggaacttaac   1440
attctgatat tccagctaaa ccaggagaag cccaaggtaa agaagaggaa gggcaagttt   1500
aagagaagtc gtttaaagct caaagatgga catcgaatca gtttaccttc agatttccag   1560
cacaagataa ccgtgcaggc ctctcccaac ttggacaaac ggcggagcct gaacagcagc   1620
agttccagtc cccgagcag ccccacaatg atgccccgac tccgagccat acagttgact    1680
tcagatgaaa gcaataaaac ttggggaagg aacacagtct ttcgacaaga agaatttgag   1740
gatgtaaaaa ggaattttaa gaaaaaaggt tgtacctggg gaccaaattc cattcaaatg   1800
aaagatagaa cagattgcaa agaaaggata agacctctct ccgatggcaa cagtccttgg   1860
tcaactatct taataaaaaa tcagaaaacc atgcccttgg cttcattgtt tgtggaccag   1920
ccagggtcct gtgaagagcc aaaactttcc cctgatggat tagaacacag aaaaccaaaa   1980
caaataaaat tgcctagtca ggcctacatt gatctacctc ttgggaaaga tgctcagaga   2040
gagaatcctg cagaagctga aagctgggag gaggcagcct ctgcgaatgc tgccacagtc   2100
tccattgaga tgactcctac gaatagtctg agtagatccc cccagagaaa gaaaacggag   2160
tcagctctgt atgggtgcac cgtccttctg gcatcggtgg ctctgggact ggacctcaga   2220
gagcttcata aagcacaggc tgctgaagaa ccgttgccca aggaagagaa gaagaaacga   2280
gagggaatct tccagcgggc ttccaagtcc cgcagaagcg ccagtcctcc cacaagcctg   2340
ccatccacct gtggggaggc cagcagccca ccctccctgc cactgtcaag tgccctgggc   2400
atcctctcca caccttcttt ctccacaaag tgcctgctgc agatggacag tgaagatcca   2460
ctggtggaca gtgcacctgt cacttgtgac tctgagatgc tcactccgga tttttgtccc   2520
actgccccag gaagtggtcg tgagccagcc ctcatgccaa gacttgacac tgattgtagt   2580
gtatcaagaa acttgccgtc ttccttccta cagcagacat gtgggaatgt accttactgt   2640
gcttcttcaa aacatagacc gtcacatcac agacggacca tgtctgatgg aaatccgacc   2700
ccaactggtg caactattat ctcagccact ggagcctctg cactgccact ctgcccctca   2760
cctgctcctc acagtcatct gccaagggag gtctcaccca agaagcacag cactgtccac   2820
atcgtgcctc agcgtcgccc tgcctccctg agaagccgct cagatctgcc tcaggcttac   2880
ccacagacag cagtgtctca gctggcacag actgcctgtg tagtgggtcg cccaggacca   2940
catcccaccc aattcctcgc tgccaaggag agaactaaat cccatgtgcc ttcattactg   3000
```

gatgctgacg tggaaggtca gagcagggac tacactgtgc c 3041

<210> SEQ ID NO 53
<211> LENGTH: 3041
<212> TYPE: DNA
<213> ORGANISM: homo sapiens

<400> SEQUENCE: 53

```
atggctttgc ggggcgccgc gggagcgacc gacaccccgg tgtcctcggc cgggggagcc     60
cccggcggct cagcgtcctc gtcgtccacc tcctcgggcg gctcggcctc ggcgggcgcg    120
gggctgtggg ccgcgctcta tgactacgag gctcgcggcg aggacgagct gagcctgcgg    180
cgcggccagc tggtggaggt gctgtcgcag gacgccgccg tgtcgggcga cgagggctgg    240
tgggcaggcc aggtgcagcg gcgcctcggc atcttccccg ccaactacgt ggctccctgc    300
cgcccggccg ccagccccgc gccgccgccc tcgcggccca gctccccggt acacgtcgcc    360
ttcgagcggc tggagctgaa ggagctcatc ggcgctgggg gcttcgggca ggtgtaccgc    420
gccacctggc agggccagga ggtggccgtg aaggcggcgc gccaggaccc ggagcaggac    480
gcggcggcgg ctgccgagag cgtgcggcgc gaggctcggc tcttcgccat gctgcggcac    540
cccaacatca tcgagctgcg cggcgtgtgc ctgcagcagc cgcacctctg cctggtgctg    600
gagttcgccc gcggcggagc gctcaaccga gcgctggccg ctgccaacgc cgccccggac    660
ccgcgcgcgc ccggcccccg ccgcgcgcgc cgcatccctc cgcacgtgct ggtcaactgg    720
gccgtgcaga tagcgcgggg catgctctac ctgcatgagg aggccttcgt gcccatcctg    780
caccgggacc tcaagtccag caacattttg ctacttgaga agatagaaca tgatgacatc    840
tgcaataaaa ctttgaagat tacagatttt gggttggaga gggaatggca caggaccacc    900
aaaatgagca cagcaggcac ctatgcctgg atggcccccg aagtgatcaa gtcttccttg    960
ttttctaagg gaagcgacat ctggagctat ggagtgctgc tgtgggaact gctcaccgga   1020
gaagtcccct atcggggcat tgatggcctc gccgtggctt atggggtagc agtcaataaa   1080
ctcactttgc ccattccatc cacctgccct gagccgtttg ccaagctcat gaaagaatgc   1140
tggcaacaag accctcatat tcgtccatcg tttgccttaa ttctcgaaca gttgactgct   1200
attgaagggg cagtgatgac tgagatgcct caagaatctt ttcattccat gcaagatgac   1260
tggaaactag aaattcaaca aatgtttgat gagttgagaa caaaggaaaa ggagctgcga   1320
tcccgggaag aggagctgac tcgggcggct ctgcagcaga agtctcagga ggagctgcta   1380
aagcggcgtg agcagcagct ggcagagcgc gagatcgacg tgctggagcg ggaacttaac   1440
attctgatat tccagctaaa ccaggagaag cccaaggtaa agaagaggaa gggcaagttt   1500
aagagaagtc gtttaaagct caaagatgga catcgaatca gtttaccttc agatttccag   1560
cacaagataa ccgtgcaggc ctctcccaac ttggacaaac ggcggagcct gaacagcagc   1620
agttccagtc ccccgagcag ccccacaatg atgccccgac tccgagccat acagttgact   1680
tcagatgaaa gcaataaaac ttggggaagg aacacagtct ttcgacaaga agaatttgag   1740
gatgtaaaaa ggaattttaa gaaaaaaggt tgtacctggg gaccaaattc cattcaaatg   1800
aaagatagaa cagattgcaa agaaaggata agacctctct ccgatggcaa cagtccttgg   1860
tcaactatct taataaaaaa tcagaaaacc atgcccttgg cttcattgtt tgtggaccag   1920
ccagggtcct gtgaagagcc aaaactttcc cctgatggat tagaacacag aaaaccaaaa   1980
caaataaaat tgcctagtca ggcctacatt gatctacctc ttgggaaaga tgctcagaga   2040
gagaatcctg cagaagctga aagctgggag gaggcagcct ctgcgaatgc tgccacagtc   2100
```

```
tccattgaga tgactcctac gaatagtctg agtagatccc cccagagaaa gaaaacggag   2160

tcagctctgt atgggtgcac cgtccttctg gcatcggtgg ctctgggact ggacctcaga   2220

gagcttcata aagcacaggc tgctgaagaa ccgttgccca aggaagagaa gaagaaacga   2280

gagggaatct tccagcgggc ttccaagtcc cgcagaagcg ccagtcctcc cacaagcctg   2340

ccatccacct gtggggaggc cagcagccca ccctccctgc cactgtcaag tgccctgggc   2400

atcctctcca caccttcttt ctccacaaag tgcctgctgc agatggacag tgaagatcca   2460

ctggtggaca gtgcacctgt cacttgtgac tctgagatgc tcactccgga tttttgtccc   2520

actgccccag gaagtggtcg tgagccagcc ctcatgccaa gacttgacac tgattgtagt   2580

gtatcaagaa acttgccgtc ttccttccta cagcagacat gtgggaatgt accttactgt   2640

gcttcttcaa aacatagacc gtcacatcac agacggacca tgtctgatgg aaatccgacc   2700

ccaactggtg caactattat ctcagccact ggagcctctg cactgccact ctgcccctca   2760

cctgctcctc acagtcatct gccaagggag gtctcaccca agaagcacag cactgtccac   2820

atcgtgcctc agcgtcgccc tgcctccctg agaagccgct cagatctgcc tcaggcttac   2880

ccacagacag cagtgtctca gctggcacag actgcctgtg tagtgggtcg cccaggacca   2940

catcccaccc aattcctcgc tgccaaggag agaactaaat cccatgtgcc ttcattactg   3000

gatgctgacg tggaaggtca gagcagggac tacactgtgc c                       3041
```

<210> SEQ ID NO 54
<211> LENGTH: 3041
<212> TYPE: DNA
<213> ORGANISM: homo sapiens

<400> SEQUENCE: 54

```
atggctttgc ggggcgccgc gggagcgacc gacaccccgg tgtcctcggc cgggggagcc     60

cccggcggct cagcgtcctc gtcgtccacc tcctcgggcg gctcggcctc ggcgggcgcg    120

gggctgtggg ccgcgctcta tgactacgag gctcgcggcg aggacgagct gagcctgcgg    180

cgcggccagc tggtggaggt gctgtcgcag gacgccgccg tgtcgggcga cgagggctgg    240

tgggcaggcc aggtgcagcg gcgcctcggc atcttccccg ccaactacgt ggctccctgc    300

cgcccggccg ccagccccgc gccgccgccc tcgcggccca gctccccggt acacgtcgcc    360

ttcgagcggc tggagctgaa ggagctcatc ggcgctgggg gcttcgggca ggtgtaccgc    420

gccacctggc agggccagga ggtggccgtg aaggcggcgc gccaggaccc ggagcaggac    480

gcggcggcgg ctgccgagag cgtgcggcgc gaggctcggc tcttcgccat gctgcggcac    540

cccaacatca tcgagctgcg cggcgtgtgc ctgcagcagc cgcacctctg cctggtgctg    600

gagttcgccc gcggcggagc gctcaaccga gcgctggccg ctgccaacgc cgccccggac    660

ccgcgcgcgc ccggcccccg ccgcgcgcgc cgcatccctc cgcacgtgct ggtcaactgg    720

gccgtgcaga tagcgcgggg catgctctac ctgcatgagg aggccttcgt gcccatcctg    780

caccgggacc tcaagtccag caacattttg ctacttgaga agatagaaca tgatgacatc    840

tgcaataaaa ctttgaagat tacagatttt gggttggcga gggaatgaca caggaccacc    900

aaaatgagca cagcaggcac ctatgcctgg atggcccccg aagtgatcaa gtcttccttg    960

ttttctaagg gaagcgacat ctggagctat ggagtgctgc tgtgggaact gctcaccgga   1020

gaagtcccct atcggggcat tgatggcctc gccgtggctt atggggtagc agtcaataaa   1080

ctcactttgc ccattccatc cacctgccct gagccgtttg ccaagctcat gaaagaatgc   1140
```

```
tggcaacaag accctcatat tcgtccatcg tttgccttaa ttctcgaaca gttgactgct   1200

attgaagggg cagtgatgac tgagatgcct caagaatctt ttcattccat gcaagatgac   1260

tggaaactag aaattcaaca aatgtttgat gagttgagaa caaaggaaaa ggagctgcga   1320

tcccgggaag aggagctgac tcgggcggct ctgcagcaga agtctcagga ggagctgcta   1380

aagcggcgtg agcagcagct ggcagagcgc gagatcgacg tgctggagcg ggaacttaac   1440

attctgatat tccagctaaa ccaggagaag cccaaggtaa agaagaggaa gggcaagttt   1500

aagagaagtc gtttaaagct caaagatgga catcgaatca gtttaccttc agatttccag   1560

cacaagataa ccgtgcaggc ctctcccaac ttggacaaac ggcggagcct gaacagcagc   1620

agttccagtc ccccgagcag ccccacaatg atgccccgac tccgagccat acagttgact   1680

tcagatgaaa gcaataaaac ttggggaagg aacacagtct ttcgacaaga agaatttgag   1740

gatgtaaaaa ggaattttaa gaaaaaaggt tgtacctggg gaccaaattc cattcaaatg   1800

aaagatagaa cagattgcaa agaaaggata agacctctct ccgatggcaa cagtccttgg   1860

tcaactatct taataaaaaa tcagaaaacc atgcccttgg cttcattgtt tgtggaccag   1920

ccagggtcct gtgaagagcc aaaactttcc cctgatggat tagaacacag aaaaccaaaa   1980

caaataaaat tgcctagtca ggcctacatt gatctacctc ttgggaaaga tgctcagaga   2040

gagaatcctg cagaagctga aagctgggag gaggcagcct ctgcgaatgc tgccacagtc   2100

tccattgaga tgactcctac gaatagtctg agtagatccc cccagagaaa gaaaacggag   2160

tcagctctgt atgggtgcac cgtccttctg gcatcggtgg ctctgggact ggacctcaga   2220

gagcttcata aagcacaggc tgctgaagaa ccgttgccca aggaagagaa gaagaaacga   2280

gagggaatct tccagcgggc ttccaagtcc cgcagaagcg ccagtcctcc cacaagcctg   2340

ccatccacct gtggggaggc cagcagccca ccctccctgc cactgtcaag tgccctgggc   2400

atcctctcca caccttcttt ctccacaaag tgcctgctgc agatggacag tgaagatcca   2460

ctggtggaca gtgcacctgt cacttgtgac tctgagatgc tcactccgga tttttgtccc   2520

actgccccag gaagtggtcg tgagccagcc ctcatgccaa gacttgacac tgattgtagt   2580

gtatcaagaa acttgccgtc ttccttccta cagcagacat gtgggaatgt accttactgt   2640

gcttcttcaa aacatagacc gtcacatcac agacggacca tgtctgatgg aaatccgacc   2700

ccaactggtg caactattat ctcagccact ggagcctctg cactgccact ctgcccctca   2760

cctgctcctc acagtcatct gccaagggag gtctcaccca agaagcacag cactgtccac   2820

atcgtgcctc agcgtcgccc tgcctccctg agaagccgct cagatctgcc tcaggcttac   2880

ccacagacag cagtgtctca gctggcacag actgcctgtg tagtgggtcg cccaggacca   2940

catcccaccc aattcctcgc tgccaaggag agaactaaat cccatgtgcc ttcattactg   3000

gatgctgacg tggaaggtca gagcagggac tacactgtgc c                       3041
```

<210> SEQ ID NO 55
<211> LENGTH: 3041
<212> TYPE: DNA
<213> ORGANISM: homo sapiens

<400> SEQUENCE: 55

```
atggctttgc ggggcgccgc gggagcgacc gacaccccgg tgtcctcggc cgggggagcc     60

cccggcggct cagcgtcctc gtcgtccacc tcctcgggcg gctcggcctc ggcgggcgcg    120

gggctgtggg ccgcgctcta tgactacgag gctcgcggcg aggacgagct gagcctgcgg    180

cgcggccagc tggtggaggt gctgtcgcag gacgccgccg tgtcgggcga cgagggctgg    240
```

```
tgggcaggcc aggtgcagcg gcgcctcggc atcttccccg ccaactacgt ggctccctgc    300
cgcccggccg ccagccccgc gccgccgccc tcgcggccca gctccccggt acacgtcgcc    360
ttcgagcggc tggagctgaa ggagctcatc ggcgctgggg gcttcgggca ggtgtaccgc    420
gccacctggc agggccagga ggtggccgtg aaggcggcgc gccaggaccc ggagcaggac    480
gcggcggcgg ctgccgagag cgtgcggcgc gaggctcggc tcttcgccat gctgcggcac    540
cccaacatca tcgagctgcg cggcgtgtgc ctgcagcagc cgcacctctg cctggtgctg    600
gagttcgccc gcggcggagc gctcaaccga gcgctggccg ctgccaacgc cgccccggac    660
ccgcgcgcgc ccggcccccg ccgcgcgcgc cgcatccctc cgcacgtgct ggtcaactgg    720
gccgtgcaga tagcgcgggg catgctctac ctgcatgagg aggccttcgt gcccatcctg    780
caccgggacc tcaagtccag caacattttg ctacttgaga agatagaaca tgatgacatc    840
tgcaataaaa ctttgaagat tacagatttt gggttggcga gggaatggca caggaccacc    900
aaaatgagca cagcaggcac ctatgcctgg atggcccccg aagtgatcaa gtcttccttg    960
ttttctaagg gaagcgacat ctggagctat ggagtgctgc tgtgggaact gctcaccgga   1020
gaagtcccct atcggggcat tgatggcctc gccgtggctt atggggtagc agtcaataaa   1080
ctcactttgc ccattccatc cacctgccct gagccgtttg ccaagctcat gaaagaatgc   1140
tggcaacaag accctcatat tcgtccatcg tttgccttaa ttctcgaaca gttgactgct   1200
attgaagggg cagtgatgac tgagatgcct caagaatctt ttcattccat gcaagatgac   1260
tggaaactag aaattcaaca aatgtttgat gagttgagaa caaaggaaaa ggagctgcga   1320
tcccgggaag aggagctgac tcgggcggct ctgcagcaga agtctcagga ggagctgcta   1380
aagcggcgtg agcagcagct ggcagagcgc gagatcgacg tgctggagcg ggaacttaac   1440
attctgatat tccagctaaa ccaggagaag cccaaggtaa agaagaggaa gggcaagttt   1500
aagagaagtc gtttaaagct caaagatgga catcgaatca gtttaccttc agatttccag   1560
cacaagataa ccgtgcaggc ctctcccaac ttggacaaac ggcggagcct gaacagcagc   1620
agttccagtc ccccgagcag ccccacaatg atgccctgac tccgagccat acagttgact   1680
tcagatgaaa gcaataaaac ttggggaagg aacacagtct ttcgacaaga agaatttgag   1740
gatgtaaaaa ggaattttaa gaaaaaaggt tgtacctggg gaccaaattc cattcaaatg   1800
aaagatagaa cagattgcaa agaaaggata agacctctct ccgatggcaa cagtccttgg   1860
tcaactatct taataaaaaa tcagaaaacc atgcccttgg cttcattgtt tgtggaccag   1920
ccagggtcct gtgaagagcc aaaactttcc cctgatggat tagaacacag aaaaccaaaa   1980
caaataaaat tgcctagtca ggcctacatt gatctacctc ttgggaaaga tgctcagaga   2040
gagaatcctg cagaagctga aagctgggag gaggcagcct ctgcgaatgc tgccacagtc   2100
tccattgaga tgactcctac gaatagtctg agtagatccc cccagagaaa gaaaacggag   2160
tcagctctgt atgggtgcac cgtccttctg gcatcggtgg ctctgggact ggacctcaga   2220
gagcttcata aagcacaggc tgctgaagaa ccgttgccca aggaagagaa gaagaaacga   2280
gagggaatct tccagcgggc ttccaagtcc cgcagaagcg ccagtcctcc cacaagcctg   2340
ccatccacct gtggggaggc cagcagccca ccctccctgc cactgtcaag tgccctgggc   2400
atcctctcca caccttcttt ctccacaaag tgcctgctgc agatggacag tgaagatcca   2460
ctggtggaca gtgcacctgt cacttgtgac tctgagatgc tcactccgga tttttgtccc   2520
actgccccag gaagtggtcg tgagccagcc ctcatgccaa gacttgacac tgattgtagt   2580
```

```
gtatcaagaa acttgccgtc ttccttccta cagcagacat gtgggaatgt accttactgt   2640

gcttcttcaa aacatagacc gtcacatcac agacggacca tgtctgatgg aaatccgacc   2700

ccaactggtg caactattat ctcagccact ggagcctctg cactgccact ctgcccctca   2760

cctgctcctc acagtcatct gccaagggag gtctcaccca agaagcacag cactgtccac   2820

atcgtgcctc agcgtcgccc tgcctccctg agaagccgct cagatctgcc tcaggcttac   2880

ccacagacag cagtgtctca gctggcacag actgcctgtg tagtgggtcg cccaggacca   2940

catcccaccc aattcctcgc tgccaaggag agaactaaat cccatgtgcc ttcattactg   3000

gatgctgacg tggaaggtca gagcagggac tacactgtgc c                       3041
```

```
<210> SEQ ID NO 56
<211> LENGTH: 3041
<212> TYPE: DNA
<213> ORGANISM: homo sapiens

<400> SEQUENCE: 56

atggctttgc ggggcgccgc gggagcgacc gacaccccgg tgtcctcggc cgggggagcc     60

cccggcggct cagcgtcctc gtcgtccacc tcctcgggcg gctcggcctc ggcgggcgcg    120

gggctgtggg ccgcgctcta tgactacgag gctcgcggcg aggacgagct gagcctgcgg    180

cgcggccagc tggtggaggt gctgtcgcag gacgccgccg tgtcgggcga cgagggctgg    240

tgggcaggcc aggtgcagcg gcgcctcggc atcttccccg ccaactacgt ggctccctgc    300

cgcccggccg ccagccccgc gccgccgccc tcgcggccca gctccccggt acacgtcgcc    360

ttcgagcggc tggagctgaa ggagctcatc ggcgctgggg gcttcgggca ggtgtaccgc    420

gccacctggc agggccagga ggtggccgtg aaggcggcgc gccaggaccc ggagcaggac    480

gcggcggcgg ctgccgagag cgtgcggcgc gaggctcggc tcttcgccat gctgcggcac    540

cccaacatca tcgagctgcg cggcgtgtgc ctgcagcagc cgcacctctg cctggtgctg    600

gagttcgccc gcggcggagc gctcaaccga gcgctggccg ctgccaacgc cgccccggac    660

ccgcgcgcgc ccggcccccg ccgcgcgcgc cgcatccctc cgcacgtgct ggtcaactgg    720

gccgtgcaga tagcgcgggg catgctctac ctgcatgagg aggccttcgt gcccatcctg    780

caccgggacc tcaagtccag caacattttg ctacttgaga agatagaaca tgatgacatc    840

tgcaataaaa ctttgaagat tacagatttt gggttggcga gggaatggca caggaccacc    900

aaaatgagca cagcaggcac ctatgcctgg atggcccccg aagtgatcaa gtcttccttg    960

ttttctaagg gaagcgacat ctggagctat ggagtgctgc tgtgggaact gctcaccgga   1020

gaagtcccct atcggggcat tgatggcctc gccgtggctt atggggtagc agtcaataaa   1080

ctcactttgc ccattccatc cacctgccct gagccgtttg ccaagctcat gaaagaatgc   1140

tggcaacaag accctcatat tcgtccatcg tttgccttaa ttctcgaaca gttgactgct   1200

attgaagggg cagtgatgac tgagatgcct caagaatctt ttcattccat gcaagatgac   1260

tggaaactag aaattcaaca aatgtttgat gagttgagaa caaaggaaaa ggagctgcga   1320

tcccgggaag aggagctgac tcgggcggct ctgcagcaga agtctcagga ggagctgcta   1380

aagcggcgtg agcagcagct ggcagagcgc gagatcgacg tgctggagcg ggaacttaac   1440

attctgatat tccagctaaa ccaggagaag cccaaggtaa agaagaggaa gggcaagttt   1500

aagagaagtc gtttaaagct caaagatgga catcgaatca gtttaccttc agatttccag   1560

cacaagataa ccgtgcaggc ctctcccaac ttggacaaac ggcggagcct gaacagcagc   1620

agttccagtc ccccgagcag ccccacaatg atgccccgac tctgagccat acagttgact   1680
```

```
tcagatgaaa gcaataaaac ttggggaagg aacacagtct ttcgacaaga agaatttgag   1740
gatgtaaaaa ggaattttaa gaaaaaaggt tgtacctggg gaccaaattc cattcaaatg   1800
aaagatagaa cagattgcaa agaaaggata agacctctct ccgatggcaa cagtccttgg   1860
tcaactatct taataaaaaa tcagaaaacc atgcccttgg cttcattgtt tgtggaccag   1920
ccagggtcct gtgaagagcc aaaactttcc cctgatggat tagaacacag aaaaccaaaa   1980
caaataaaat tgcctagtca ggcctacatt gatctacctc ttgggaaaga tgctcagaga   2040
gagaatcctg cagaagctga aagctgggag gaggcagcct ctgcgaatgc tgccacagtc   2100
tccattgaga tgactcctac gaatagtctg agtagatccc cccagagaaa gaaaacggag   2160
tcagctctgt atgggtgcac cgtccttctg gcatcggtgg ctctgggact ggacctcaga   2220
gagcttcata aagcacaggc tgctgaagaa ccgttgccca aggaagagaa gaagaaacga   2280
gagggaatct tccagcgggc ttccaagtcc cgcagaagcg ccagtcctcc cacaagcctg   2340
ccatccacct gtggggaggc cagcagccca ccctccctgc cactgtcaag tgccctgggc   2400
atcctctcca caccttcttt ctccacaaag tgcctgctgc agatggacag tgaagatcca   2460
ctggtggaca gtgcacctgt cacttgtgac tctgagatgc tcactccgga tttttgtccc   2520
actgccccag gaagtggtcg tgagccagcc ctcatgccaa gacttgacac tgattgtagt   2580
gtatcaagaa acttgccgtc ttccttccta cagcagacat gtgggaatgt accttactgt   2640
gcttcttcaa aacatagacc gtcacatcac agacggacca tgtctgatgg aaatccgacc   2700
ccaactggtg caactattat ctcagccact ggagcctctg cactgccact ctgcccctca   2760
cctgctcctc acagtcatct gccaagggag gtctcaccca agaagcacag cactgtccac   2820
atcgtgcctc agcgtcgccc tgcctccctg agaagccgct cagatctgcc tcaggcttac   2880
ccacagacag cagtgtctca gctggcacag actgcctgtg tagtgggtcg cccaggacca   2940
catcccaccc aattcctcgc tgccaaggag agaactaaat cccatgtgcc ttcattactg   3000
gatgctgacg tggaaggtca gagcagggac tacactgtgc c                       3041
```

```
<210> SEQ ID NO 57
<211> LENGTH: 3041
<212> TYPE: DNA
<213> ORGANISM: homo sapiens

<400> SEQUENCE: 57
```

```
atggctttgc ggggcgccgc gggagcgacc gacaccccgg tgtcctcggc cgggggagcc     60
cccggcggct cagcgtcctc gtcgtccacc tcctcgggcg gctcggcctc ggcgggcgcg    120
gggctgtggg ccgcgctcta tgactacgag gctcgcggcg aggacgagct gagcctgcgg    180
cgcggccagc tggtggaggt gctgtcgcag gacgccgccg tgtcgggcga cgagggctgg    240
tgggcaggcc aggtgcagcg gcgcctcggc atcttccccg ccaactacgt ggctccctgc    300
cgcccggccg ccagccccgc gccgccgccc tcgcggccca gctccccggt acacgtcgcc    360
ttcgagcggc tggagctgaa ggagctcatc ggcgctgggg gcttcgggca ggtgtaccgc    420
gccacctggc agggccagga ggtggccgtg aaggcggcgc gccaggaccc ggagcaggac    480
gcggcggcgg ctgccgagag cgtgcggcgc gaggctcggc tcttcgccat gctgcggcac    540
cccaacatca tcgagctgcg cggcgtgtgc ctgcagcagc cgcacctctg cctggtgctg    600
gagttcgccc gcggcggagc gctcaaccga gcgctggccg ctgccaacgc cgccccggac    660
ccgcgcgcgc ccggcccccg ccgcgcgcgc cgcatccctc cgcacgtgct ggtcaactgg    720
```

-continued

```
gccgtgcaga tagcgcgggg catgctctac ctgcatgagg aggccttcgt gcccatcctg    780
caccgggacc tcaagtccag caacattttg ctacttgaga agatagaaca tgatgacatc    840
tgcaataaaa ctttgaagat tacagatttt gggttggcga gggaatggca caggaccacc    900
aaaatgagca cagcaggcac ctatgcctgg atggcccccg aagtgatcaa gtcttccttg    960
ttttctaagg gaagcgacat ctggagctat ggagtgctgc tgtgggaact gctcaccgga   1020
gaagtcccct atcggggcat tgatggcctc gccgtggctt atggggtagc agtcaataaa   1080
ctcactttgc ccattccatc cacctgccct gagccgtttg ccaagctcat gaaagaatgc   1140
tggcaacaag accctcatat tcgtccatcg tttgccttaa ttctcgaaca gttgactgct   1200
attgaagggg cagtgatgac tgagatgcct caagaatctt ttcattccat gcaagatgac   1260
tggaaactag aaattcaaca aatgtttgat gagttgagaa caaaggaaaa ggagctgcga   1320
tcccgggaag aggagctgac tcgggcggct ctgcagcaga agtctcagga ggagctgcta   1380
aagcggcgtg agcagcagct ggcagagcgc gagatcgacg tgctggagcg ggaacttaac   1440
attctgatat tccagctaaa ccaggagaag cccaaggtaa agaagaggaa gggcaagttt   1500
aagagaagtc gtttaaagct caaagatgga catcgaatca gtttaccttc agatttccag   1560
cacaagataa ccgtgcaggc ctctcccaac ttggacaaac ggcggagcct gaacagcagc   1620
agttccagtc cccgagcag ccccacaatg atgccccgac tccgagccat acagttgact   1680
tcagatgaaa gcaataaaac ttggggaagg aacacagtct ttcgacaaga agaatttgag   1740
gatgtaaaaa ggaattttaa gaaaaaaggt tgtacctggg gaccaatttc cattcaaatg   1800
aaagatagaa cagattgcaa agaaaggata agacctctct ccgatggcaa cagtccttgg   1860
tcaactatct taataaaaaa tcagaaaacc atgcccttgg cttcattgtt tgtggaccag   1920
ccagggtcct gtgaagagcc aaaactttcc cctgatggat tagaacacag aaaaccaaaa   1980
caaataaaat tgcctagtca ggcctacatt gatctacctc ttgggaaaga tgctcagaga   2040
gagaatcctg cagaagctga aagctgggag gaggcagcct ctgcgaatgc tgccacagtc   2100
tccattgaga tgactcctac gaatagtctg agtagatccc cccagagaaa gaaaacggag   2160
tcagctctgt atgggtgcac cgtccttctg gcatcggtgg ctctgggact ggacctcaga   2220
gagcttcata aagcacaggc tgctgaagaa ccgttgccca aggaagagaa gaagaaacga   2280
gagggaatct tccagcgggc ttccaagtcc cgcagaagcg ccagtcctcc cacaagcctg   2340
ccatccacct gtggggaggc cagcagccca ccctccctgc cactgtcaag tgccctgggc   2400
atcctctcca caccttcttt ctccacaaag tgcctgctgc agatggacag tgaagatcca   2460
ctggtggaca gtgcacctgt cacttgtgac tctgagatgc tcactccgga tttttgtccc   2520
actgccccag gaagtggtcg tgagccagcc ctcatgccaa gacttgacac tgattgtagt   2580
gtatcaagaa acttgccgtc ttccttccta cagcagacat gtgggaatgt accttactgt   2640
gcttcttcaa aacatagacc gtcacatcac agacggacca tgtctgatgg aaatccgacc   2700
ccaactggtg caactattat ctcagccact ggagcctctg cactgccact ctgcccctca   2760
cctgctcctc acagtcatct gccaagggag gtctcaccca agaagcacag cactgtccac   2820
atcgtgcctc agcgtcgccc tgcctccctg agaagccgct cagatctgcc tcaggcttac   2880
ccacagacag cagtgtctca gctggcacag actgcctgtg tagtgggtcg cccaggacca   2940
catcccaccc aattcctcgc tgccaaggag agaactaaat cccatgtgcc ttcattactg   3000
gatgctgacg tggaaggtca gagcagggac tacactgtgc c                       3041
```

<210> SEQ ID NO 58
<211> LENGTH: 3041
<212> TYPE: DNA
<213> ORGANISM: homo sapiens

<400> SEQUENCE: 58

```
atggctttgc ggggcgccgc gggagcgacc gacaccccgg tgtcctcggc cgggggagcc     60
cccggcggct cagcgtcctc gtcgtccacc tcctcgggcg gctcggcctc ggcgggcgcg    120
gggctgtggg ccgcgctcta tgactacgag gctcgcggcg aggacgagct gagcctgcgg    180
cgcggccagc tggtggaggt gctgtcgcag gacgccgccg tgtcgggcga cgagggctgg    240
tgggcaggcc aggtgcagcg gcgcctcggc atcttccccg ccaactacgt ggctccctgc    300
cgcccggccg ccagccccgc gccgccgccc tcgcggccca gctccccggt acacgtcgcc    360
ttcgagcggc tggagctgaa ggagctcatc ggcgctgggg gcttcgggca ggtgtaccgc    420
gccacctggc agggccagga ggtggccgtg aaggcggcgc gccaggaccc ggagcaggac    480
gcggcggcgg ctgccgagag cgtgcggcgc gaggctcggc tcttcgccat gctgcggcac    540
cccaacatca tcgagctgcg cggcgtgtgc ctgcagcagc cgcacctctg cctggtgctg    600
gagttcgccc gcggcggagc gctcaaccga gcgctggccg ctgccaacgc cgccccggac    660
ccgcgcgcgc ccggccccccg ccgcgcgcgc cgcatccctc cgcacgtgct ggtcaactgg    720
gccgtgcaga tagcgcgggg catgctctac ctgcatgagg aggccttcgt gcccatcctg    780
caccgggacc tcaagtccag caacattttg ctacttgaga agatagaaca tgatgacatc    840
tgcaataaaa ctttgaagat tacagatttt gggttggcga gggaatggca caggaccacc    900
aaaatgagca cagcaggcac ctatgcctgg atggcccccg aagtgatcaa gtcttccttg    960
ttttctaagg gaagcgacat ctggagctat ggagtgctgc tgtgggaact gctcaccgga   1020
gaagtcccct atcggggcat tgatggcctc gccgtggctt atggggtagc agtcaataaa   1080
ctcactttgc ccattccatc cacctgccct gagccgtttg ccaagctcat gaaagaatgc   1140
tggcaacaag accctcatat tcgtccatcg tttgccttaa ttctcgaaca gttgactgct   1200
attgaagggg cagtgatgac tgagatgcct caagaatctt ttcattccat gcaagatgac   1260
tggaaactag aaattcaaca aatgtttgat gagttgagaa caaaggaaaa ggagctgcga   1320
tcccgggaag aggagctgac tcgggcggct ctgcagcaga agtctcagga ggagctgcta   1380
aagcggcgtg agcagcagct ggcagagcgc gagatcgacg tgctggagcg ggaacttaac   1440
attctgatat tccagctaaa ccaggagaag cccaaggtaa agaagaggaa gggcaagttt   1500
aagagaagtc gtttaaagct caaagatgga catcgaatca gtttaccttc agatttccag   1560
cacaagataa ccgtgcaggc ctctcccaac ttggacaaac ggcggagcct gaacagcagc   1620
agttccagtc ccccgagcag ccccacaatg atgccccgac tccgagccat acagttgact   1680
tcagatgaaa gcaataaaac ttggggaagg aacacagtct ttcgacaaga agaatttgag   1740
gatgtaaaaa ggaattttaa gaaaaaaggt tgtacctggg gaccaaattc cattcaaatg   1800
aaagatagaa cagattgcaa agaaaggata agacctctct ccgatggcaa cagtccttgg   1860
tcaactatct taataaaaaa tcaggaaacc atgcccttgg cttcattgtt tgtggaccag   1920
ccagggtcct gtgaagagcc aaaactttcc cctgatggat tagaacacag aaaaccaaaa   1980
caaataaaat tgcctagtca ggcctacatt gatctacctc ttgggaaaga tgctcagaga   2040
gagaatcctg cagaagctga aagctgggag gaggcagcct ctgcgaatgc tgccacagtc   2100
tccattgaga tgactcctac gaatagtctg agtagatccc cccagagaaa gaaaacggag   2160
```

```
tcagctctgt atgggtgcac cgtccttctg gcatcggtgg ctctgggact ggacctcaga   2220

gagcttcata aagcacaggc tgctgaagaa ccgttgccca aggaagagaa gaagaaacga   2280

gagggaatct tccagcgggc ttccaagtcc cgcagaagcg ccagtcctcc cacaagcctg   2340

ccatccacct gtggggaggc cagcagccca ccctccctgc cactgtcaag tgccctgggc   2400

atcctctcca caccttcttt ctccacaaag tgcctgctgc agatggacag tgaagatcca   2460

ctggtggaca gtgcacctgt cacttgtgac tctgagatgc tcactccgga tttttgtccc   2520

actgccccag gaagtggtcg tgagccagcc ctcatgccaa gacttgacac tgattgtagt   2580

gtatcaagaa acttgccgtc ttccttccta cagcagacat gtgggaatgt accttactgt   2640

gcttcttcaa aacatagacc gtcacatcac agacggacca tgtctgatgg aaatccgacc   2700

ccaactggtg caactattat ctcagccact ggagcctctg cactgccact ctgcccctca   2760

cctgctcctc acagtcatct gccaagggag gtctcaccca agaagcacag cactgtccac   2820

atcgtgcctc agcgtcgccc tgcctccctg agaagccgct cagatctgcc tcaggcttac   2880

ccacagacag cagtgtctca gctggcacag actgcctgtg tagtgggtcg cccaggacca   2940

catcccaccc aattcctcgc tgccaaggag agaactaaat cccatgtgcc ttcattactg   3000

gatgctgacg tggaaggtca gagcagggac tacactgtgc c                        3041
```

<210> SEQ ID NO 59
<211> LENGTH: 3041
<212> TYPE: DNA
<213> ORGANISM: homo sapiens

<400> SEQUENCE: 59

```
atggctttgc ggggcgccgc gggagcgacc gacaccccgg tgtcctcggc cgggggagcc     60

cccggcggct cagcgtcctc gtcgtccacc tcctcgggcg gctcggcctc ggcgggcgcg    120

gggctgtggg ccgcgctcta tgactacgag gctcgcggcg aggacgagct gagcctgcgg    180

cgcggccagc tggtggaggt gctgtcgcag gacgccgccg tgtcgggcga cgagggctgg    240

tgggcaggcc aggtgcagcg gcgcctcggc atcttccccg ccaactacgt ggctccctgc    300

cgcccggccg ccagccccgc gccgccgccc tcgcggccca gctccccggt acacgtcgcc    360

ttcgagcggc tggagctgaa ggagctcatc ggcgctgggg gcttcgggca ggtgtaccgc    420

gccacctggc agggccagga ggtggccgtg aaggcggcgc gccaggaccc ggagcaggac    480

gcggcggcgg ctgccgagag cgtgcggcgc gaggctcggc tcttcgccat gctgcggcac    540

cccaacatca tcgagctgcg cggcgtgtgc ctgcagcagc cgcacctctg cctggtgctg    600

gagttcgccc gcggcggagc gctcaaccga gcgctggccg ctgccaacgc cgccccggac    660

ccgcgcgcgc ccggcccccg ccgcgcgcgc cgcatccctc cgcacgtgct ggtcaactgg    720

gccgtgcaga tagcgcgggg catgctctac ctgcatgagg aggccttcgt gcccatcctg    780

caccgggacc tcaagtccag caacattttg ctacttgaga agatagaaca tgatgacatc    840

tgcaataaaa ctttgaagat tacagatttt gggttggcga gggaatggca caggaccacc    900

aaaatgagca cagcaggcac ctatgcctgg atggcccccg aagtgatcaa gtcttccttg    960

ttttctaagg gaagcgacat ctggagctat ggagtgctgc tgtgggaact gctcaccgga   1020

gaagtcccct atcggggcat tgatggcctc gccgtggctt atggggtagc agtcaataaa   1080

ctcactttgc ccattccatc cacctgccct gagccgtttg ccaagctcat gaaagaatgc   1140

tggcaacaag accctcatat tcgtccatcg tttgccttaa ttctcgaaca gttgactgct   1200

attgaagggg cagtgatgac tgagatgcct caagaatctt ttcattccat gcaagatgac   1260
```

```
tggaaactag aaattcaaca aatgtttgat gagttgagaa caaaggaaaa ggagctgcga   1320

tcccgggaag aggagctgac tcgggcggct ctgcagcaga agtctcagga ggagctgcta   1380

aagcggcgtg agcagcagct ggcagagcgc gagatcgacg tgctggagcg ggaacttaac   1440

attctgatat tccagctaaa ccaggagaag cccaaggtaa agaagaggaa gggcaagttt   1500

aagagaagtc gtttaaagct caaagatgga catcgaatca gtttaccttc agatttccag   1560

cacaagataa ccgtgcaggc ctctcccaac ttggacaaac ggcggagcct gaacagcagc   1620

agttccagtc cccgagcag ccccacaatg atgccccgac tccgagccat acagttgact   1680

tcagatgaaa gcaataaaac ttggggaagg aacacagtct ttcgacaaga agaatttgag   1740

gatgtaaaaa ggaattttaa gaaaaaaggt tgtacctggg gaccaaattc cattcaaatg   1800

aaagatagaa cagattgcaa agaaaggata agacctctct ccgatggcaa cagtccttgg   1860

tcaactatct taataaaaaa tcagaaaacc atgcccttgg cttcattgtt tgtggaccag   1920

ccagggtcct gtgaagagcc aaaactttcc cctgatggat tagaacacag aaaaccaaaa   1980

caaataaaat tgcctagtca ggcctacatt gatctacctc ttgggaaaga tgctcagaga   2040

gagaatcctg cagaagctga aagctgggag gaggcagcct ctgcgaatgc tgccacagtc   2100

tccattgaga tgactcctac gaatagtctg agtagatccc cccagagaaa gaaaacggag   2160

tcagctctgt atgggtgcac cgtccttctg gcatcggtgg ctctgggact ggacctcaga   2220

gagcttcata aagcacaggc tgctgaagaa ccgttgccca aggaagagaa gaagaaacga   2280

gagggaatct tccagcgggc ttccaagtcc cgcagaagcg ccagtcctcc cacaagcctg   2340

ccatccacct gtggggaggc cagcagccca ccctccctgc cactgtcaag tgccctgggc   2400

atcctctcca caccttcttt ctccacaaag tgcctgctgc agatggacag tgaagatcca   2460

ctggtggaca gtgcacctgt cacttgtgac tctgagatgc tcactccgga tttttgtccc   2520

actgcctcag gaagtggtcg tgagccagcc ctcatgccaa gacttgacac tgattgtagt   2580

gtatcaagaa acttgccgtc ttccttccta cagcagacat gtgggaatgt accttactgt   2640

gcttcttcaa aacatagacc gtcacatcac agacggacca tgtctgatgg aaatccgacc   2700

ccaactggtg caactattat ctcagccact ggagcctctg cactgccact ctgcccctca   2760

cctgctcctc acagtcatct gccaagggag gtctcaccca agaagcacag cactgtccac   2820

atcgtgcctc agcgtcgccc tgcctccctg agaagccgct cagatctgcc tcaggcttac   2880

ccacagacag cagtgtctca gctggcacag actgcctgtg tagtgggtcg cccaggacca   2940

catcccaccc aattcctcgc tgccaaggag agaactaaat cccatgtgcc ttcattactg   3000

gatgctgacg tggaaggtca gagcagggac tacactgtgc c                       3041
```

<210> SEQ ID NO 60
<211> LENGTH: 3041
<212> TYPE: DNA
<213> ORGANISM: homo sapiens

<400> SEQUENCE: 60

```
atggctttgc ggggcgccgc gggagcgacc gacaccccgg tgtcctcggc cgggggagcc     60

cccggcggct cagcgtcctc gtcgtccacc tcctcgggcg gctcggcctc ggcgggcgcg    120

gggctgtggg ccgcgctcta tgactacgag gctcgcggcg aggacgagct gagcctgcgg    180

cgcggccagc tggtggaggt gctgtcgcag gacgccgccg tgtcgggcga cgagggctgg    240

tgggcaggcc aggtgcagcg gcgcctcggc atcttccccg ccaactacgt ggctccctgc    300
```

-continued

```
cgcccggccg ccagccccgc gccgccgccc tcgcggccca gctccccggt acacgtcgcc    360

ttcgagcggc tggagctgaa ggagctcatc ggcgctgggg gcttcgggca ggtgtaccgc    420

gccacctggc agggccagga ggtggccgtg aaggcggcgc gccaggaccc ggagcaggac    480

gcggcggcgg ctgccgagag cgtgcggcgc gaggctcggc tcttcgccat gctgcggcac    540

cccaacatca tcgagctgcg cggcgtgtgc ctgcagcagc cgcacctctg cctggtgctg    600

gagttcgccc gcggcggagc gctcaaccga gcgctggccg ctgccaacgc cgccccggac    660

ccgcgcgcgc ccggcccccg ccgcgcgcgc cgcatccctc cgcacgtgct ggtcaactgg    720

gccgtgcaga tagcgcgggg catgctctac ctgcatgagg aggccttcgt gcccatcctg    780

caccgggacc tcaagtccag caacattttg ctacttgaga agatagaaca tgatgacatc    840

tgcaataaaa ctttgaagat tacagatttt gggttggcga gggaatggca caggaccacc    900

aaaatgagca cagcaggcac ctatgcctgg atggcccccg aagtgatcaa gtcttccttg    960

ttttctaagg gaagcgacat ctggagctat ggagtgctgc tgtgggaact gctcaccgga   1020

gaagtcccct atcggggcat tgatggcctc gccgtggctt atggggtagc agtcaataaa   1080

ctcactttgc ccattccatc cacctgccct gagccgtttg ccaagctcat gaaagaatgc   1140

tggcaacaag accctcatat tcgtccatcg tttgccttaa ttctcgaaca gttgactgct   1200

attgaagggg cagtgatgac tgagatgcct caagaatctt ttcattccat gcaagatgac   1260

tggaaactag aaattcaaca aatgtttgat gagttgagaa caaaggaaaa ggagctgcga   1320

tcccgggaag aggagctgac tcgggcggct ctgcagcaga agtctcagga ggagctgcta   1380

aagcggcgtg agcagcagct ggcagagcgc gagatcgacg tgctggagcg ggaacttaac   1440

attctgatat tccagctaaa ccaggagaag cccaaggtaa agaagaggaa gggcaagttt   1500

aagagaagtc gtttaaagct caaagatgga catcgaatca gtttaccttc agatttccag   1560

cacaagataa ccgtgcaggc ctctcccaac ttggacaaac ggcggagcct gaacagcagc   1620

agttccagtc cccgagcag ccccacaatg atgccccgac tccgagccat acagttgact    1680

tcagatgaaa gcaataaaac ttggggaagg aacacagtct ttcgacaaga agaatttgag   1740

gatgtaaaaa ggaattttaa gaaaaaaggt tgtacctggg gaccaaattc cattcaaatg   1800

aaagatagaa cagattgcaa agaaaggata agacctctct ccgatggcaa cagtccttgg   1860

tcaactatct taataaaaaa tcagaaaacc atgcccttgg cttcattgtt tgtggaccag   1920

ccagggtcct gtgaagagcc aaaactttcc cctgatggat tagaacacag aaaaccaaaa   1980

caaataaaat tgcctagtca ggcctacatt gatctacctc ttgggaaaga tgctcagaga   2040

gagaatcctg cagaagctga aagctgggag gaggcagcct ctgcgaatgc tgccacagtc   2100

tccattgaga tgactcctac gaatagtctg agtagatccc cccagagaaa gaaaacggag   2160

tcagctctgt atgggtgcac cgtccttctg gcatcggtgg ctctgggact ggacctcaga   2220

gagcttcata aagcacaggc tgctgaagaa ccgttgccca aggaagagaa gaagaaacga   2280

gagggaatct tccagcgggc ttccaagtcc cgcagaagcg ccagtcctcc cacaagcctg   2340

ccatccacct gtggggaggc cagcagccca ccctccctgc cactgtcaag tgccctgggc   2400

atcctctcca caccttcttt ctccacaaag tgcctgctgc agatggacag tgaagatcca   2460

ctggtggaca gtgcacctgt cacttgtgac tctgagatgc tcactccgga tttttgtccc   2520

actgccccag gaagtggtcg tgagccagcc ctcatgccaa gacttgacac tgattgtagt   2580

gtatcaagaa acttgccgtc ttccttccta cagcagacat gtgggaatgt accttactgt   2640

gcttcttcaa aacatagacc gtcacatccc agacggacca tgtctgatgg aaatccgacc   2700
```

```
ccaactggtg caactattat ctcagccact ggagcctctg cactgccact ctgcccctca   2760

cctgctcctc acagtcatct gccaagggag gtctcaccca agaagcacag cactgtccac   2820

atcgtgcctc agcgtcgccc tgcctccctg agaagccgct cagatctgcc tcaggcttac   2880

ccacagacag cagtgtctca gctggcacag actgcctgtg tagtgggtcg cccaggacca   2940

catcccaccc aattcctcgc tgccaaggag agaactaaat cccatgtgcc ttcattactg   3000

gatgctgacg tggaaggtca gagcagggac tacactgtgc c                        3041


<210> SEQ ID NO 61
<211> LENGTH: 3041
<212> TYPE: DNA
<213> ORGANISM: homo sapiens

<400> SEQUENCE: 61

atggctttgc ggggcgccgc gggagcgacc gacaccccgg tgtcctcggc cgggggagcc     60

cccggcggct cagcgtcctc gtcgtccacc tcctcgggcg gctcggcctc ggcgggcgcg    120

gggctgtggg ccgcgctcta tgactacgag gctcgcggcg aggacgagct gagcctgcgg    180

cgcggccagc tggtggaggt gctgtcgcag gacgccgccg tgtcgggcga cgagggctgg    240

tgggcaggcc aggtgcagcg gcgcctcggc atcttccccg ccaactacgt ggctccctgc    300

cgcccggccg ccagccccgc gccgccgccc tcgcggccca gctccccggt acacgtcgcc    360

ttcgagcggc tggagctgaa ggagctcatc ggcgctgggg gcttcgggca ggtgtaccgc    420

gccacctggc agggccagga ggtggccgtg aaggcggcgc gccaggaccc ggagcaggac    480

gcggcggcgg ctgccgagag cgtgcggcgc gaggctcggc tcttcgccat gctgcggcac    540

cccaacatca tcgagctgcg cggcgtgtgc ctgcagcagc cgcacctctg cctggtgctg    600

gagttcgccc gcggcggagc gctcaaccga gcgctggccg ctgccaacgc cgccccggac    660

ccgcgcgcgc ccggcccccg ccgcgcgcgc cgcatccctc cgcacgtgct ggtcaactgg    720

gccgtgcaga tagcgcgggg catgctctac ctgcatgagg aggccttcgt gcccatcctg    780

caccgggacc tcaagtccag caacattttg ctacttgaga agatagaaca tgatgacatc    840

tgcaataaaa ctttgaagat tacagatttt gggttggcga gggaatggca caggaccacc    900

aaaatgagca cagcaggcac ctatgcctgg atggcccccg aagtgatcaa gtcttccttg    960

ttttctaagg gaagcgacat ctggagctat ggagtgctgc tgtgggaact gctcaccgga   1020

gaagtcccct atcggggcat tgatggcctc gccgtggctt atggggtagc agtcaataaa   1080

ctcactttgc ccattccatc cacctgccct gagccgtttg ccaagctcat gaaagaatgc   1140

tggcaacaag accctcatat tcgtccatcg tttgccttaa ttctcgaaca gttgactgct   1200

attgaagggg cagtgatgac tgagatgcct caagaatctt ttcattccat gcaagatgac   1260

tggaaactag aaattcaaca aatgtttgat gagttgagaa caaaggaaaa ggagctgcga   1320

tcccgggaag aggagctgac tcgggcggct ctgcagcaga agtctcagga ggagctgcta   1380

aagcggcgtg agcagcagct ggcagagcgc gagatcgacg tgctggagcg ggaacttaac   1440

attctgatat tccagctaaa ccaggagaag cccaaggtaa agaagaggaa gggcaagttt   1500

aagagaagtc gtttaaagct caaagatgga catcgaatca gtttaccttc agatttccag   1560

cacaagataa ccgtgcaggc ctctcccaac ttggacaaac ggcggagcct gaacagcagc   1620

agttccagtc ccccgagcag ccccacaatg atgccccgac tccgagccat acagttgact   1680

tcagatgaaa gcaataaaac ttggggaagg aacacagtct ttcgacaaga agaatttgag   1740
```

-continued

```
gatgtaaaaa ggaattttaa gaaaaaaggt tgtacctggg gaccaaattc cattcaaatg   1800

aaagatagaa cagattgcaa agaaaggata agacctctct ccgatggcaa cagtccttgg   1860

tcaactatct taataaaaaa tcagaaaacc atgcccttgg cttcattgtt tgtggaccag   1920

ccagggtcct gtgaagagcc aaaactttcc cctgatggat tagaacacag aaaaccaaaa   1980

caaataaaat tgcctagtca ggcctacatt gatctacctc ttgggaaaga tgctcagaga   2040

gagaatcctg cagaagctga aagctgggag gaggcagcct ctgcgaatgc tgccacagtc   2100

tccattgaga tgactcctac gaatagtctg agtagatccc cccagagaaa gaaaacggag   2160

tcagctctgt atgggtgcac cgtccttctg gcatcggtgg ctctgggact ggacctcaga   2220

gagcttcata aagcacaggc tgctgaagaa ccgttgccca aggaagagaa gaagaaacga   2280

gagggaatct tccagcgggc ttccaagtcc cgcagaagcg ccagtcctcc cacaagcctg   2340

ccatccacct gtggggaggc cagcagccca ccctccctgc cactgtcaag tgccctgggc   2400

atcctctcca caccttcttt ctccacaaag tgcctgctgc agatggacag tgaagatcca   2460

ctggtggaca gtgcacctgt cacttgtgac tctgagatgc tcactccgga tttttgtccc   2520

actgccccag gaagtggtcg tgagccagcc ctcatgccaa gacttgacac tgattgtagt   2580

gtatcaagaa acttgccgtc ttccttccta cagcagacat gtgggaatgt accttactgt   2640

gcttcttcaa aacatagacc gtcacatcac agacggacca cgtctgatgg aaatccgacc   2700

ccaactggtg caactattat ctcagccact ggagcctctg cactgccact ctgcccctca   2760

cctgctcctc acagtcatct gccaagggag gtctcaccca agaagcacag cactgtccac   2820

atcgtgcctc agcgtcgccc tgcctccctg agaagccgct cagatctgcc tcaggcttac   2880

ccacagacag cagtgtctca gctggcacag actgcctgtg tagtgggtcg cccaggacca   2940

catcccaccc aattcctcgc tgccaaggag agaactaaat cccatgtgcc ttcattactg   3000

gatgctgacg tggaaggtca gagcagggac tacactgtgc c                        3041
```